(12) United States Patent
Shelton, IV et al.

(10) Patent No.: US 8,137,267 B2
(45) Date of Patent: Mar. 20, 2012

(54) RETRACTOR WITH FLEXIBLE SLEEVE

(75) Inventors: Frederick E. Shelton, IV, Hillsboro, OH (US); Christopher W. Widenhouse, Clarksville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 283 days.

(21) Appl. No.: 12/420,107

(22) Filed: Apr. 8, 2009

(65) Prior Publication Data

US 2010/0261970 A1    Oct. 14, 2010

(51) Int. Cl.
*A61B 1/32* (2006.01)
(52) U.S. Cl. ........................................ 600/203; 600/208
(58) Field of Classification Search ............ 600/201–209
See application file for complete search history.

(56) References Cited

U.S. PATENT DOCUMENTS

| | | |
|---|---|---|
| 2,129,391 A | 9/1938 | Wappler |
| 3,402,710 A | 9/1968 | Paleschuck |
| 3,654,965 A | 4/1972 | Gramain |
| 4,112,932 A | 9/1978 | Chiulli |
| 4,306,545 A | 12/1981 | Ivan et al. |
| 4,379,458 A | 4/1983 | Bauer et al. |
| 4,402,683 A | 9/1983 | Kopman |
| 4,417,888 A | 11/1983 | Cosentino et al. |
| 5,010,925 A | 4/1991 | Atkinson et al. |
| 5,091,435 A | 2/1992 | Suzuki et al. |
| 5,183,471 A | 2/1993 | Wilk |
| 5,197,955 A | 3/1993 | Stephens et al. |
| 5,207,213 A | 5/1993 | Auhll et al. |
| 5,209,737 A | 5/1993 | Ritchart et al. |
| 5,209,741 A | 5/1993 | Spaeth |
| 5,235,966 A | 8/1993 | Jamner |
| 5,269,772 A | 12/1993 | Wilk |
| 5,308,336 A | 5/1994 | Hart et al. |

(Continued)

FOREIGN PATENT DOCUMENTS

DE    19814576 A1    10/1999

(Continued)

OTHER PUBLICATIONS

International Search Report and Written Opinion for International App. No. PCT/US2010/036811 dated Sep. 14, 2010 (6 pages).
International Search Report, from PCT/US10/36829, mailed Sep. 9, 2010 (5 pages).
European Search Report, EP 10250732, dated Jul. 28, 2010.
International Search Report and Written Opinion for Application No. PCT/US2010/037190, dated Sep. 22, 2010 (15 pages).

(Continued)

*Primary Examiner* — Eduardo C Robert
*Assistant Examiner* — Jacqueline Johanas
(74) *Attorney, Agent, or Firm* — Nutter McClennen & Fish LLP

(57) ABSTRACT

Devices and methods are disclosed for accessing a body cavity or other surgical site while providing optimal device length and improved tissue retraction, device retention and stability, and seal integrity. A surgical access device is disclosed that generally comprises an external seal housing having at least one working channel and that is coupled to a flexible and/or resilient retractor. The retractor can include a resilient ring at its distal circumference configured to be deformed to facilitate insertion through an incision and then to return to an undeformed state having a diameter greater than a diameter of the incision once within a body cavity. Various means of coupling the retractor to the housing are disclosed, as are various types of seals that can be included within the housing. "Low-profile"and "peel-away cannula" embodiments of the surgical access device are disclosed, along with methods of accessing a body cavity using such devices.

13 Claims, 15 Drawing Sheets

U.S. PATENT DOCUMENTS

| | | |
|---|---|---|
| 5,312,417 A | 5/1994 | Wilk |
| 5,320,611 A | 6/1994 | Bonutti et al. |
| 5,342,315 A | 8/1994 | Rowe et al. |
| 5,366,478 A | 11/1994 | Brinkerhoff et al. |
| 5,385,553 A | 1/1995 | Hart et al. |
| 5,385,560 A | 1/1995 | Wulf |
| 5,391,154 A | 2/1995 | Young |
| 5,431,676 A | 7/1995 | Dubrul et al. |
| 5,443,452 A | 8/1995 | Hart et al. |
| 5,443,484 A | 8/1995 | Kirsch et al. |
| 5,476,475 A | 12/1995 | Gadberry |
| 5,480,410 A | 1/1996 | Cuschieri et al. |
| 5,531,758 A | 7/1996 | Uschold et al. |
| 5,545,179 A | 8/1996 | Williamson, IV |
| 5,562,677 A | 10/1996 | Hildwein et al. |
| 5,569,205 A | 10/1996 | Hart et al. |
| 5,569,254 A | 10/1996 | Carlson et al. |
| 5,584,850 A | 12/1996 | Hart et al. |
| 5,628,732 A | 5/1997 | Antoon, Jr. et al. |
| 5,634,911 A | 6/1997 | Hermann et al. |
| 5,634,937 A | 6/1997 | Mollenauer et al. |
| 5,643,301 A | 7/1997 | Mollenauer |
| 5,653,705 A | 8/1997 | de la Torre et al. |
| 5,653,718 A | 8/1997 | Yoon |
| 5,672,168 A | 9/1997 | de la Torre et al. |
| 5,676,657 A | 10/1997 | Yoon |
| 5,695,448 A | 12/1997 | Kimura et al. |
| 5,707,359 A | 1/1998 | Bufalini |
| 5,752,970 A | 5/1998 | Yoon |
| 5,782,812 A | 7/1998 | Hart et al. |
| 5,797,888 A | 8/1998 | Yoon |
| 5,803,919 A | 9/1998 | Hart et al. |
| 5,814,058 A | 9/1998 | Carlson et al. |
| 5,827,319 A | 10/1998 | Carlson et al. |
| 5,843,040 A | 12/1998 | Exline |
| 5,865,807 A | 2/1999 | Blake, III |
| 5,868,762 A | 2/1999 | Cragg et al. |
| 5,882,344 A | 3/1999 | Stouder, Jr. |
| 5,891,013 A | 4/1999 | Thompson |
| 5,899,208 A | 5/1999 | Bonadio |
| 5,906,577 A | 5/1999 | Beane et al. |
| 5,946,280 A | 8/1999 | Ohkubo |
| 5,957,913 A | 9/1999 | de la Torre et al. |
| 5,990,382 A | 11/1999 | Fox |
| 5,997,515 A | 12/1999 | de la Torre et al. |
| 6,024,736 A | 2/2000 | de la Torre et al. |
| RE36,702 E | 5/2000 | Green et al. |
| 6,056,766 A | 5/2000 | Thompson et al. |
| 6,066,090 A | 5/2000 | Yoon |
| 6,077,288 A | 6/2000 | Shimomura et al. |
| 6,080,174 A | 6/2000 | Dubrul et al. |
| 6,086,603 A | 7/2000 | Termin et al. |
| 6,120,513 A | 9/2000 | Bailey et al. |
| 6,123,689 A | 9/2000 | To et al. |
| 6,142,396 A | 11/2000 | Gallus |
| 6,142,936 A | 11/2000 | Beane et al. |
| 6,162,196 A | 12/2000 | Hart et al. |
| 6,217,555 B1 | 4/2001 | Hart et al. |
| 6,245,052 B1 | 6/2001 | Orth et al. |
| 6,258,069 B1 | 7/2001 | Carpentier et al. |
| 6,277,064 B1 | 8/2001 | Yoon |
| 6,315,770 B1 | 11/2001 | de la Torre et al. |
| 6,319,246 B1 | 11/2001 | de la Torre et al. |
| 6,325,812 B1 | 12/2001 | Dubrul et al. |
| 6,348,034 B1 | 2/2002 | Thompson |
| 6,352,503 B1 | 3/2002 | Matsui et al. |
| 6,440,061 B1 | 8/2002 | Wenner et al. |
| 6,440,063 B1 | 8/2002 | Beane et al. |
| 6,447,489 B1 | 9/2002 | Peterson |
| 6,454,783 B1 | 9/2002 | Piskun |
| 6,458,077 B1 | 10/2002 | Boebel et al. |
| 6,488,620 B1 | 12/2002 | Segermark et al. |
| 6,551,270 B1 | 4/2003 | Bimbo et al. |
| 6,551,282 B1 | 4/2003 | Exline et al. |
| 6,589,167 B1 | 7/2003 | Shimomura et al. |
| 6,605,063 B2 | 8/2003 | Bousquet |
| 6,669,674 B1 | 12/2003 | Macoviak et al. |
| 6,702,787 B2 | 3/2004 | Racenet et al. |
| 6,706,033 B1 | 3/2004 | Martinez et al. |
| 6,706,050 B1 | 3/2004 | Giannadakis |
| 6,908,430 B2 | 6/2005 | Caldwell et al. |
| 6,939,296 B2 | 9/2005 | Ewers et al. |
| 6,945,932 B1 | 9/2005 | Caldwell et al. |
| 6,972,026 B1 | 12/2005 | Caldwell et al. |
| 7,014,628 B2 | 3/2006 | Bousquet |
| 7,052,454 B2 | 5/2006 | Taylor |
| 7,083,626 B2 | 8/2006 | Hart et al. |
| 7,118,528 B1 | 10/2006 | Piskun |
| 7,163,510 B2 | 1/2007 | Kahle et al. |
| 7,163,525 B2 | 1/2007 | Franer |
| 7,214,185 B1 | 5/2007 | Rosney et al. |
| 7,229,408 B2 | 6/2007 | Douglas et al. |
| 7,338,473 B2 | 3/2008 | Campbell et al. |
| 7,344,547 B2 | 3/2008 | Piskun |
| 7,371,227 B2 | 5/2008 | Zeiner |
| 7,393,322 B2 | 7/2008 | Wenchell |
| 7,449,011 B2 | 11/2008 | Wenchell et al. |
| 7,481,795 B2 | 1/2009 | Thompson et al. |
| 7,867,164 B2 * | 1/2011 | Butler et al. .................. 600/208 |
| 2002/0156432 A1 | 10/2002 | Racenet et al. |
| 2003/0028179 A1 | 2/2003 | Piskun |
| 2003/0139756 A1 | 7/2003 | Brustad |
| 2003/0216770 A1 | 11/2003 | Persidsky et al. |
| 2004/0015185 A1 | 1/2004 | Ewers et al. |
| 2004/0019322 A1 | 1/2004 | Hoffmann |
| 2004/0082969 A1 | 4/2004 | Kerr |
| 2004/0106942 A1 | 6/2004 | Taylor et al. |
| 2004/0117032 A1 | 6/2004 | Roth |
| 2004/0138528 A1 | 7/2004 | Richter et al. |
| 2004/0199121 A1 | 10/2004 | Wenchell et al. |
| 2004/0215063 A1 | 10/2004 | Bonadio et al. |
| 2004/0230160 A1 | 11/2004 | Blanco |
| 2004/0230161 A1 | 11/2004 | Zeiner |
| 2004/0254426 A1 | 12/2004 | Wenchell |
| 2005/0020884 A1 | 1/2005 | Hart et al. |
| 2005/0033342 A1 | 2/2005 | Hart et al. |
| 2005/0085842 A1 | 4/2005 | Eversull et al. |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0192483 A1 | 9/2005 | Bonadio et al. |
| 2005/0209608 A1 | 9/2005 | O'Heeron |
| 2005/0215862 A1 | 9/2005 | Larson et al. |
| 2005/0216028 A1 | 9/2005 | Hart et al. |
| 2005/0222582 A1 | 10/2005 | Wenchell |
| 2005/0267419 A1 | 12/2005 | Smith |
| 2005/0273132 A1 | 12/2005 | Shluzas et al. |
| 2005/0277946 A1 | 12/2005 | Greenhalgh |
| 2005/0288558 A1 * | 12/2005 | Ewers et al. .................. 600/206 |
| 2006/0012965 A1 | 1/2006 | Beall et al. |
| 2006/0019592 A1 | 1/2006 | Kupferberg et al. |
| 2006/0019723 A1 | 1/2006 | Vorenkamp et al. |
| 2006/0020241 A1 | 1/2006 | Piskun et al. |
| 2006/0020281 A1 | 1/2006 | Smith |
| 2006/0021061 A1 | 1/2006 | Cerri et al. |
| 2006/0021891 A1 | 2/2006 | Franer et al. |
| 2006/0025813 A1 | 2/2006 | Shelton et al. |
| 2006/0030755 A1 * | 2/2006 | Ewers et al. .................. 600/206 |
| 2006/0071432 A1 | 4/2006 | Staudner |
| 2006/0129165 A1 | 6/2006 | Edoga et al. |
| 2006/0212061 A1 | 9/2006 | Wenchell |
| 2006/0212062 A1 | 9/2006 | Farascioni |
| 2006/0217665 A1 | 9/2006 | Prosek |
| 2006/0224129 A1 | 10/2006 | Beasley et al. |
| 2006/0224164 A1 | 10/2006 | Hart et al. |
| 2006/0229501 A1 | 10/2006 | Jensen et al. |
| 2006/0241651 A1 | 10/2006 | Wilk |
| 2006/0241671 A1 | 10/2006 | Greenhalgh |
| 2006/0247498 A1 | 11/2006 | Bonadio et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0258899 A1 | 11/2006 | Gill et al. |
| 2006/0264706 A1 | 11/2006 | Piskun |
| 2006/0270911 A1 | 11/2006 | Voegele et al. |

| | | | |
|---|---|---|---|
| 2007/0049966 A1 | 3/2007 | Bonadio et al. | |
| 2007/0060939 A1 | 3/2007 | Lancial et al. | |
| 2007/0085232 A1 | 4/2007 | Brustad et al. | |
| 2007/0088202 A1* | 4/2007 | Albrecht et al. ............. | 600/201 |
| 2007/0088204 A1 | 4/2007 | Albrecht et al. | |
| 2007/0088258 A1 | 4/2007 | Wenchell et al. | |
| 2007/0088277 A1 | 4/2007 | McGinley et al. | |
| 2007/0118021 A1 | 5/2007 | Pokorney | |
| 2007/0118175 A1 | 5/2007 | Butler et al. | |
| 2007/0151566 A1 | 7/2007 | Kahle et al. | |
| 2007/0185453 A1 | 8/2007 | Michael et al. | |
| 2007/0208312 A1 | 9/2007 | Norton et al. | |
| 2007/0255219 A1* | 11/2007 | Vaugh et al. ............. | 604/167.02 |
| 2008/0009797 A1 | 1/2008 | Stellon et al. | |
| 2008/0025519 A1 | 1/2008 | Yu et al. | |
| 2008/0027476 A1 | 1/2008 | Piskun | |
| 2008/0051739 A1 | 2/2008 | McFarlane | |
| 2008/0058728 A1 | 3/2008 | Soltz et al. | |
| 2008/0065021 A1 | 3/2008 | Jenkins et al. | |
| 2008/0086080 A1 | 4/2008 | Mastri et al. | |
| 2008/0119821 A1 | 5/2008 | Agnihotri et al. | |
| 2008/0132765 A1 | 6/2008 | Beckman et al. | |
| 2008/0255519 A1 | 10/2008 | Piskun et al. | |
| 2008/0281161 A1 | 11/2008 | Albrecht et al. | |
| 2009/0005799 A1 | 1/2009 | Franer et al. | |
| 2009/0082731 A1 | 3/2009 | Moreno | |
| 2009/0118587 A1 | 5/2009 | Voegele et al. | |
| 2009/0187079 A1 | 7/2009 | Albrecht et al. | |
| 2009/0270685 A1 | 10/2009 | Moreno et al. | |
| 2009/0270686 A1 | 10/2009 | Duke et al. | |
| 2009/0270818 A1 | 10/2009 | Duke | |
| 2010/0010310 A1 | 1/2010 | Weisenburgh, II et al. | |
| 2010/0081863 A1 | 4/2010 | Hess et al. | |
| 2010/0081864 A1 | 4/2010 | Hess et al. | |
| 2010/0081871 A1 | 4/2010 | Widenhouse et al. | |
| 2010/0081880 A1 | 4/2010 | Widenhouse et al. | |
| 2010/0081881 A1 | 4/2010 | Murray et al. | |
| 2010/0081882 A1 | 4/2010 | Hess et al. | |
| 2010/0081883 A1 | 4/2010 | Murray et al. | |
| 2010/0081995 A1 | 4/2010 | Widenhouse et al. | |
| 2010/0228090 A1 | 9/2010 | Weisenburgh, II et al. | |
| 2010/0228091 A1 | 9/2010 | Widenhouse et al. | |
| 2010/0228092 A1 | 9/2010 | Ortiz et al. | |
| 2010/0228094 A1 | 9/2010 | Ortiz et al. | |
| 2010/0228096 A1 | 9/2010 | Weisenburgh, II et al. | |
| 2010/0228198 A1 | 9/2010 | Widenhouse et al. | |
| 2010/0249525 A1 | 9/2010 | Shelton, IV et al. | |
| 2010/0261970 A1 | 10/2010 | Shelton, IV et al. | |
| 2010/0261972 A1 | 10/2010 | Widenhouse et al. | |
| 2010/0261974 A1 | 10/2010 | Shelton, IV et al. | |
| 2010/0262080 A1 | 10/2010 | Shelton, IV et al. | |
| 2010/0268162 A1 | 10/2010 | Shelton, IV et al. | |
| 2010/0274093 A1 | 10/2010 | Shelton, IV | |
| 2010/0280327 A1 | 11/2010 | Nobis et al. | |
| 2010/0312060 A1 | 12/2010 | Widenhouse et al. | |
| 2010/0312061 A1 | 12/2010 | Hess et al. | |
| 2010/0312062 A1 | 12/2010 | Cropper et al. | |
| 2010/0312063 A1 | 12/2010 | Hess et al. | |
| 2010/0312064 A1 | 12/2010 | Weisenburgh, II et al. | |
| 2010/0312065 A1 | 12/2010 | Shelton, IV et al. | |
| 2010/0312066 A1 | 12/2010 | Cropper et al. | |
| 2010/0312189 A1 | 12/2010 | Shelton, IV et al. | |

FOREIGN PATENT DOCUMENTS

| | | |
|---|---|---|
| DE | 20022005 U1 | 4/2001 |
| EP | 568383 A1 | 11/1993 |
| EP | 577400 A1 | 1/1994 |
| EP | 0637431 A1 | 2/1995 |
| EP | 646358 A1 | 4/1995 |
| EP | 709918 | 5/1996 |
| EP | 0776231 B1 | 6/1997 |
| EP | 950376 | 10/1999 |
| EP | 1219251 A1 | 7/2002 |
| EP | 1219252 A1 | 7/2002 |
| EP | 1219253 A1 | 7/2002 |
| EP | 1350476 | 10/2003 |
| EP | 1702575 A2 | 9/2006 |
| EP | 1731105 A1 | 12/2006 |
| EP | 1774918 A1 | 4/2007 |
| EP | 2119404 A1 | 11/2009 |
| FR | 2710270 A1 | 3/1995 |
| JP | 2006320750 | 11/2006 |
| WO | 9407552 | 4/1994 |
| WO | 9407552 A1 | 4/1994 |
| WO | 9602297 A1 | 2/1996 |
| WO | 9608897 A1 | 3/1996 |
| WO | 9636283 A1 | 11/1996 |
| WO | 9743958 A1 | 11/1997 |
| WO | 0032263 A1 | 6/2000 |
| WO | 0041759 A1 | 7/2000 |
| WO | 0108563 A2 | 2/2001 |
| WO | 0217800 A2 | 3/2002 |
| WO | 2004030515 A2 | 4/2004 |
| WO | 2005000454 A1 | 1/2005 |
| WO | 2005002454 A1 | 1/2005 |
| WO | 2005087112 A1 | 9/2005 |
| WO | 2005094432 A2 | 10/2005 |
| WO | 2005097019 A2 | 10/2005 |
| WO | 2005097234 A2 | 10/2005 |
| WO | 2006057982 A2 | 6/2006 |
| WO | 2007008741 A1 | 1/2007 |
| WO | 2007119232 A2 | 10/2007 |
| WO | 2008024502 A2 | 2/2008 |
| WO | 2008028149 A2 | 3/2008 |
| WO | 2008121294 A1 | 10/2008 |
| WO | 2009035663 A2 | 3/2009 |

OTHER PUBLICATIONS

"Surgeon performs single-port laparoscopic surgery > Kidney removal with instructions inserted through single port access SPA > One Port Umbilicus Surgery OPUS > Uretero-pelvic junction repair > Bilateral pyeloplasy > Triport > Quadport > R-Port laparoscopic access device > Advanced Surgical Concepts ASC" Ideas For Surgery.com, Dec. 2007, 4 pages.

Desai, Mihir M. et al., "Laparoscopic and Robtic Urology—Scarless single port transumbilical nephrectomy and pyeloplasty: first clinical report," Journal Compilation, 2008 BJU International, 101, pp. 83-88.

Lee D, et al. Novel Approach to Minimizing Trocar Sites during Challenging Hand-Assisted Laparoscopic Surgery Utilizing the GelPort: Trans-Gel Instrument and Utilization, Journal of Endourology, vol. 17, No. 2, Mar. 2003, pp. 69-71.

Nakajima K, et al. Hand-assisted laparoscopic colorectal surgery using GelPort, Surg Endosc. Jan. 2004; 18(1)102-5. Epub Sep. 10, 2003.

Nakajima K, et al. Use of the surgical towel in colorectal hand-assisted laparoscopic surgery (HALS), Surg Endosc. Mar. 2004; 18(3):552-3.

Patel, R. et al. "Hand-Assisted Laparoscopic Devices: The Second Generation," Journal of Endourology, vol. 18, No. 7, Sep. 2004, pp: 649-653.

Rane, A. et al., "Single-Port Access Nephrectomy and Other Laparoscopic Urologic Procedures Using a Novel Laparoscopic Port (R-Port)," Urology, Aug. 2008; 72(2):260-264.

International Search Report and Written Opinion for Application No. PCT/US2010/036806, dated Sep. 3, 2010 (8 pages).

International Search Report and Written Opinion for Application No. PCT/US2010/036820, dated Oct. 22, 2010 (18 pages).

U.S. Appl. No. 12/242,333, filed Sep. 30, 2008.
U.S. Appl. No. 12/242,353, filed Sep. 30, 2008.
U.S. Appl. No. 12/242,381, filed Sep. 30, 2008.
U.S. Appl. No. 12/242,711, filed Sep. 30, 2008.
U.S. Appl. No. 12/242,721, filed Sep. 30, 2008.
U.S. Appl. No. 12/242,726, filed Sep. 30, 2008.
U.S. Appl. No. 12/242,765, filed Sep. 30, 2008.
U.S. Appl. No. 12/399,482, filed Mar. 6, 2009.
U.S. Appl. No. 12/399,547, filed Mar. 6, 2009.
U.S. Appl. No. 12/399,625, filed Mar. 6, 2009.
U.S. Appl. No. 12/420,202, filed Apr. 8, 2009.
U.S. Appl. No. 12/420,232, filed Apr. 8, 2009.
U.S. Appl. No. 12/420,146, filed Apr. 8, 2009.

* cited by examiner

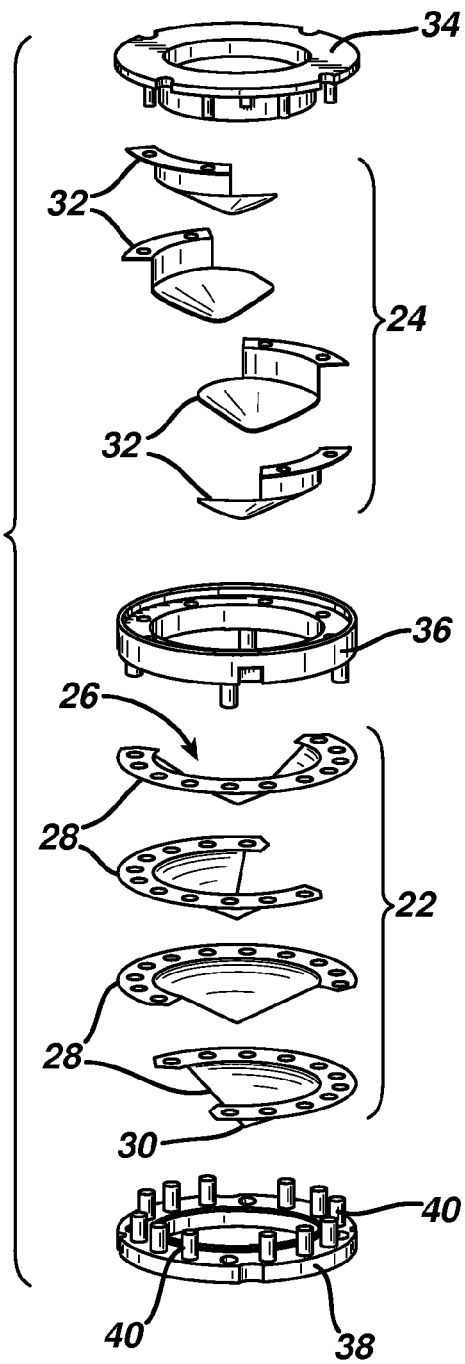
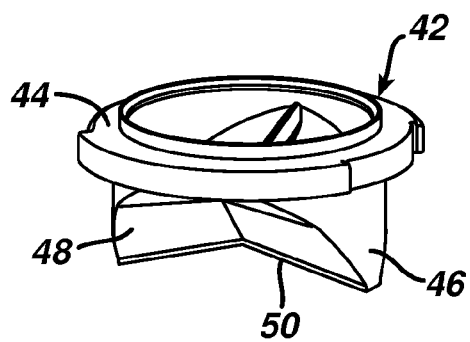

RETRACTOR WITH FLEXIBLE SLEEVE

FIELD OF THE INVENTION

The present invention relates to methods and devices for performing surgical procedures, and in particular to methods and devices for accessing a body cavity.

BACKGROUND OF THE INVENTION

In many surgical procedures, it is desirable to provide one or more working channels into a body cavity through which various instruments can be passed to view, engage, and/or treat tissue to achieve a diagnostic or therapeutic effect. In laparoscopic abdominal procedures for example, the abdominal cavity is generally insufflated with $CO_2$ gas to a pressure of around 15 mm Hg. The abdominal wall is pierced and one or more tubular cannulas, each defining a working channel, are inserted into the abdominal cavity. A laparoscopic telescope connected to an operating room monitor can be used to visualize the operative field and can be placed through one of the working channels. Other laparoscopic instruments such as graspers, dissectors, scissors, retractors, etc. can also be placed through one or more of the working channels to facilitate various manipulations by the surgeon and/or surgical assistant(s).

One problem with existing methods and devices is that the thickness of abdominal tissue which must be traversed by the cannula varies from patient to patient. As a result, when working with fixed length devices, a variety of different length cannulas are required to be on hand and the surgeon must estimate the thickness of the abdominal tissue for the particular patient and then select a cannula having the proper length. This process is cumbersome and can result in the insertion of cannulas that have an excess length within the patient. When cannulas are placed in close proximity to each other, such excess cannula length can cause interference between working channels and the instruments passed therethrough. The excess length can potentially cause damage to patient tissue if the excess length is significant.

Another drawback to existing access devices is that they do not retract tissue beyond the initial incision to any appreciable degree. Instead, they generally have a rigid body with a straight tubular shape that dramatically limits the range of angles at which surgical instruments can be positioned when passed therethrough. Angulation of such instruments thus requires angulation of the entire access device, which can cause these existing devices to suffer from decreased retention and stability and from poor seal integrity between the access device and adjacent tissue. Sutures, stability threads, deployment anchor mechanisms, and collars have been developed in an attempt to address these concerns, however further improvements would be desirable, particularly for smaller-diameter access devices or where extreme angulation is required.

Accordingly, there is a need for surgical access methods and devices that provide optimal device length and improved tissue retraction, tissue wall retention, stability, and seal integrity.

SUMMARY OF THE INVENTION

The methods and devices disclosed herein can be useful to access a body cavity while providing optimal device length, improved tissue retraction, improved retention and stability of the device in tissue, and improved seal integrity.

In one exemplary embodiment, a surgical access device is provided. The surgical access device can include a housing having a proximal external portion and an elongate implantable distal portion with at least one working channel extending therebetween, the housing being configured to receive at least one surgical instrument for passage into the working channel. The device can further include a flexible elongate sleeve coaxial with the housing and matable to and extending over a portion of the implantable distal portion such that the sleeve extends distally from the implantable distal portion and a resilient and flexible annular ring at the distal circumference of the sleeve, wherein the annular ring has a diameter in its undeformed state that is greater than a diameter of the sleeve and the implantable distal portion. The annular ring can optionally include a resilient member disposed therein.

The implantable distal portion of the housing can be matable to the sleeve in a variety of ways. In one embodiment, the implantable distal portion can have at least one surface feature on an exterior thereof, such as a thread and/or a raised ridge, configured to engage the sleeve. The device can further include at least one collar configured to be disposed around the sleeve and the implantable distal portion to assist in mating the sleeve to the housing. The collar can take a variety of forms, comprising for example an elastic o-ring and/or two matable halves. The shape and size of the elongate sleeve is not particularly limited, and in one embodiment the distal portion of the elongate sleeve can be flared such that it has a diameter greater than a diameter of a proximal portion thereof.

The housing can include at least one instrument port formed therein, the at least one instrument port being in communication with the working channel and having at least one seal element formed therein. The seal element can be effective to provide a substantially fluid tight seal with a surgical instrument when the surgical instrument is present in the instrument port. In another embodiment, the seal element is configured to provide a substantially fluid tight seal when the surgical instrument is not present in the instrument port.

In another embodiment, the surgical access device can comprise a semi-rigid cannula having at least an implantable portion and a flexible and resilient retractor extending distally from the cannula and coupled along a length of the implantable portion of the cannula at a seal region. The seal region can be configured to form a seal with tissue along a sidewall of an opening in a tissue layer, and the retractor can include a distal portion terminating in an annular ring that is configured to expand radially within a body cavity beneath the tissue layer such that the distal portion of the retractor has a diameter greater than the cannula and is configured to abut the tissue layer. The seal region can optionally be configured to be positioned about halfway through the tissue layer. The implantable portion can have at least one surface feature formed on an exterior thereof configured to engage the retractor, such as a thread and/or a raised ridge. The surgical access device can further include at least one collar configured to be disposed around the retractor and the implantable portion to assist in mating the retractor to the cannula.

The cannula can also include at least one instrument port formed therein, the instrument port having at least one seal element formed therein that can be effective to provide a substantially fluid tight seal with a surgical instrument when the surgical instrument is present in the instrument port. In another embodiment, the seal is configured to provide a substantially fluid tight seal when the surgical instrument is not present in the instrument port. The distal potion of the retractor can be flared such that is has a diameter greater than a diameter of a proximal portion thereof.

In another exemplary embodiment, a method for providing access through tissue to a body cavity is provided. The method can include providing a housing having an external portion, an elongate implantable portion, and a flexible and resilient retractor extending over a length of the implantable portion at a seal region. The housing, implantable portion and retractor can define a working channel that terminates in a resilient annular ring at a distal portion of the flexible retractor, and the annular ring can have a diameter in an undeformed state that is greater than the diameter of the implantable portion. The method can also include implanting the housing by deforming the retractor such that it is able to pass through an opening in a tissue layer, positioning the housing such that the implantable portion extends at least partially into the opening in the tissue layer creating a seal between a tissue wall defining the opening and the seal region, and allowing the annular ring to return to the undeformed state distal to the tissue layer. In certain embodiments, the annular ring can abut a portion of the tissue layer. In addition, the external portion of the housing can abut an exterior surface of the tissue layer.

BRIEF DESCRIPTION OF THE DRAWINGS

The invention will be more fully understood from the following detailed description taken in conjunction with the accompanying drawings, in which:

FIG. 3 is an exploded perspective view of one embodiment of an instrument seal;

FIG. 4 is a perspective view of one embodiment of a zero-closure seal;

DETAILED DESCRIPTION OF THE INVENTION

Figure 1:
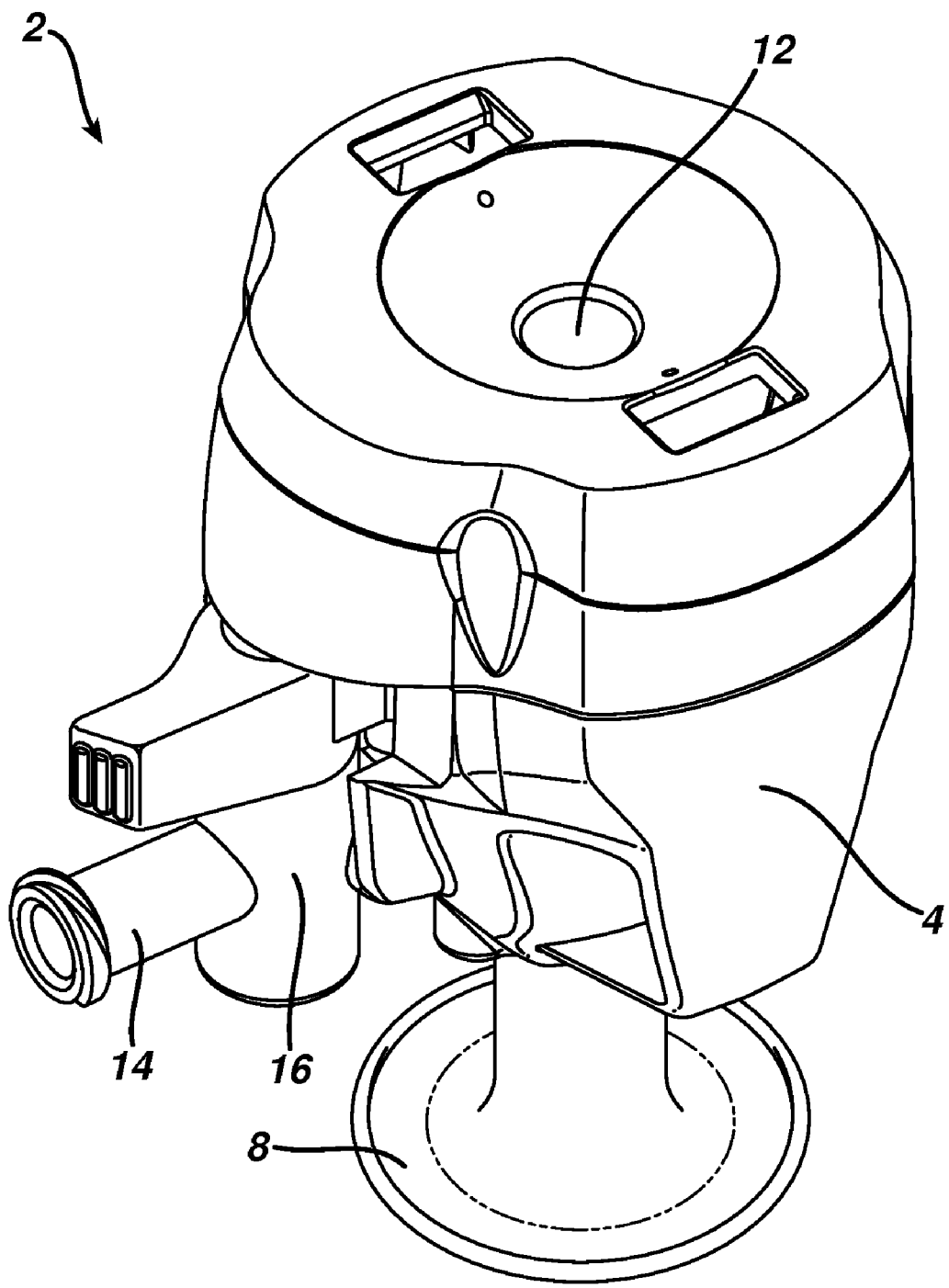
FIG. 1 is a perspective view of one embodiment of a surgical access device with a flexible retractor.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

A person skilled in the art will appreciate that, while methods and devices are described herein in connection with minimally invasive laparoscopic procedures in the abdominal cavity, the methods and devices can be used in almost any part of a human or animal body and in various other types of surgical procedures. By way of non-limiting example, the devices and methods disclosed herein can be used in the thoracic cavity, pelvic cavity, cranial cavity and/or any of the body's natural orifices and can be used in endoscopic procedures and/or in open surgical procedures.

In general, devices and methods are provided for accessing a body cavity while providing optimal device length, improved tissue retraction, improved retention and stability of the device in tissue, and improved seal integrity. In one embodiment, a seal housing with one or more working channels defined therein is provided with an implantable rigid or semi-rigid cannula at its distal end. A flexible and elastic sleeve extends distally from the cannula and terminates in an annular ring at the sleeve's distal circumference. The annular ring can be deformable, allowing it to be inserted into a small opening or incision in a patient's abdominal wall and resilient, allowing it to return back to its undeformed state, or a state approaching its undeformed state, once inside the abdominal wall and distal to the peritoneum. The annular ring can be sized such that its diameter in an undeformed state is greater than the diameter of the tissue opening and the sleeve can be sized to have a length that approximates the thickness of the abdominal wall. When so sized, the strain and/or tension applied to the elastic sleeve by the resilient ring causes the sleeve to be stretched against the inner wall of the tissue opening, thereby significantly improving the retention and stability of the access device. The force exerted by the stretched sleeve against the surrounding tissue can obviate the need for traditional stability devices such as suturing or other tie-down features on the external portion of the housing. In addition, the stretching and contraction of the sleeve and annular ring accommodates a broad spectrum of abdominal wall thicknesses and leaves no excess cannula length extending into the abdominal cavity, and can thereby optimize device length for almost any application. The strain of the sleeve against the adjacent tissue also provides improved retraction, opening the distal portion of the incision to a greater volume and giving the surgeon more room to manipulate instruments and, in particular, a greater ability to angulate instruments with respect to the abdominal wall. This strain also provides improved seal integrity between the exterior of the cannula and/or sleeve and the surrounding tissue by maintaining tight contact even when the access device is angulated or flexed significantly with respect to the patient.

Figure 2:
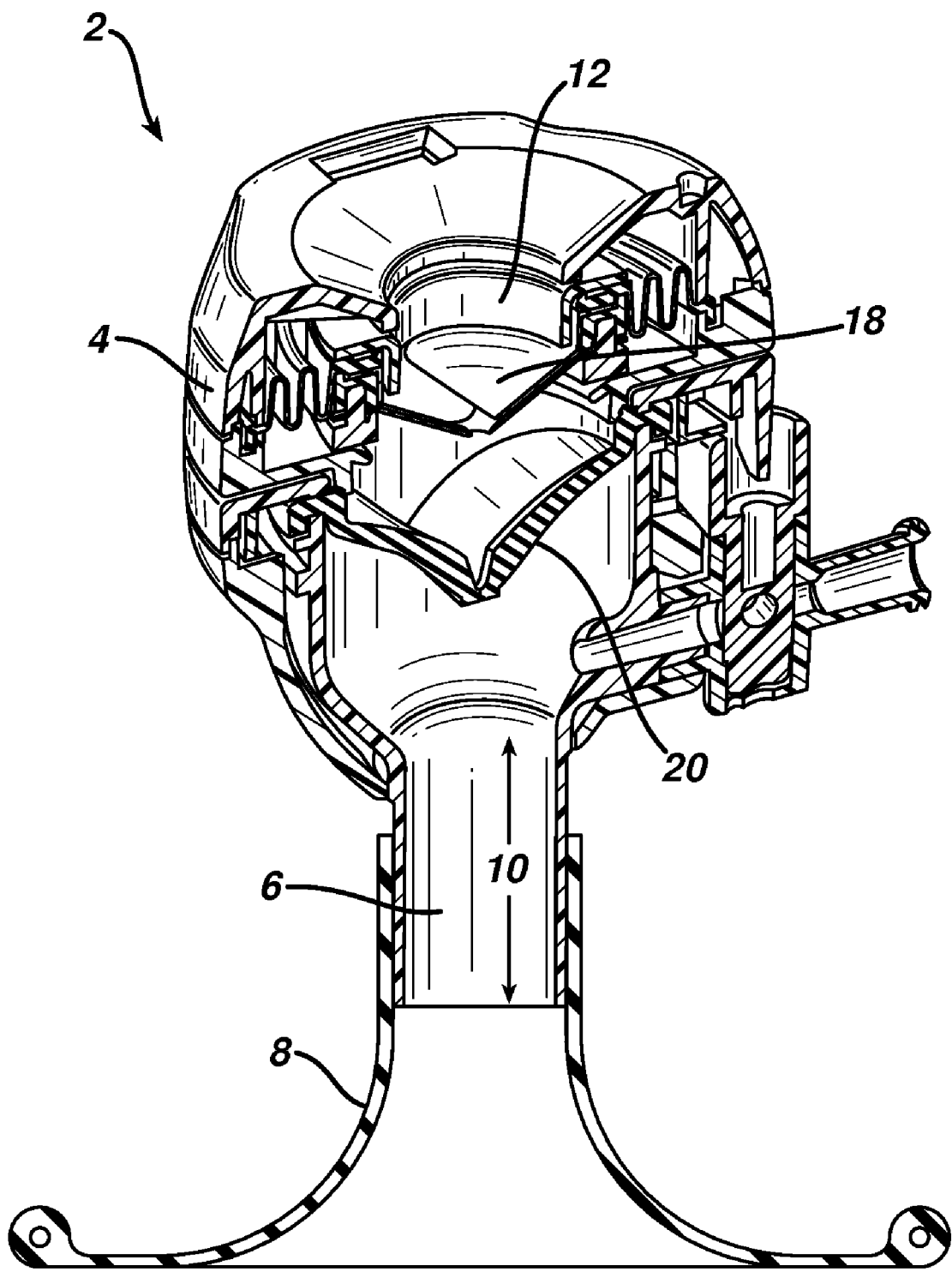
FIG. 2 is a cross-sectional view of the surgical access device of FIG. 1.

FIGS. 1 and 2 illustrate one exemplary embodiment of a surgical access device 2. As shown, the surgical access device 2 is generally in the form of a housing having an external proximal portion 4 (also referred to herein as a proximal housing) that can house one or more sealing elements, an intermediate cannula 6 extending distally from the proximal housing 4 and configured to be implanted in tissue, and a distal retractor 8 extending distally from the cannula. The surgical access device 2 defines a working channel 10 extending completely therethrough for introducing various instruments into a body cavity. While the illustrated embodiment includes only one working channel, the surgical access device can also be a multi-port device having a plurality of working channels.

A number of configurations are available for the proximal housing 4. In the embodiment illustrated in FIGS. 1 and 2, the proximal housing 4 has a generally cylindrical shape. An opening 12 can be formed in the proximal end of the housing 4 such that the opening 12 is coaxial with the working channel 10 extending through the housing 4, the cannula 6, and the retractor 8. The housing 4 can also include other features, such as a luer connector 14 and a stop-cock valve 16 for allowing and preventing the passage of an insufflation fluid, e.g. carbon dioxide, through the surgical access device 2 and into a body cavity. The cannula 6 can also have various configurations, and can include various features known in the art. In the illustrated embodiment, the cannula 6 has a generally elongate cylindrical shape. One skilled in the art will appreciate that the housing 4 and the cannula 6 can be formed as a unitary structure or as two separate components that are mated to one another. Where the housing 4 and cannula 6 are a unitary structure, the cannula 6 can be considered as a distal portion of the housing 4 or the housing 4 can be considered a proximal portion of the cannula 6. The cannula and/or housing can be formed from a variety of materials known in the art, including but not limited to various polymers, including polycarbonates and polyetheretherketone (PEEK), metals such as titanium or stainless steel, composites such as carbon-fiber reinforced PEEK, various ceramic materials, and/or any combination thereof. The cannula and/or housing can also be formed of various semi-rigid/flexible materials, including polyurethanes such as Pellethane (available from The Dow Chemical Company of Midland, Mich., USA), thermoplastic elastomers such as Santoprene (available from ExxonMobil Chemical of Houston, Tex., USA), polyisoprene elastomers, medium to high durometer silicone elastomers, and/or any combination thereof. In one embodiment, the proximal housing can have a length of about 15-20 mm. The cannula can have a diameter of about 5-12 mm and a length that varies depending upon the requirements of a surgical procedure and the size of the patient. In one embodiment, the length of the cannula is in the range of about 15-20 mm (for abdominal walls having a thickness less than 4 cm). The cannula can also have a length in the range of about 20-30 mm (for abdominal walls having a thickness of 4-7 cm).

Typically, during surgical procedures in a body cavity such as the abdomen, insufflation is provided through the surgical access device 2 to expand the body cavity to facilitate the surgical procedure. In order to maintain insufflation within the body cavity, the housing 4 and or cannula 6 can include at least one seal disposed therein to prevent fluid from escaping. Various seal configurations are known in the art, but typically the surgical access device includes an instrument seal that forms a seal around an instrument inserted therethrough, but otherwise does not form a seal when no instrument is inserted therethrough, a trocar seal or zero-closure seal that seals the working channel when no instrument is inserted therethrough, or a combination instrument seal and trocar seal that is effective to both form a seal around an instrument inserted therethrough and to form a seal in the working channel when no instrument is inserted therethrough. In the embodiment shown in FIGS. 1 and 2, the surgical access device 2 includes an instrument seal 18 and a separate trocar or zero-closure seal 20. A person skilled in the art will appreciate, however, that various other seals known in the art can be used including for example, flapper valves, gel seals, diaphragm seals, etc.

The instrument seal 18 is shown in more detail in FIG. 3. As shown, the instrument seal 18 is generally in the form of a multi-layer protective member 24 disposed on a proximal surface 26 of a multi-layer conical seal 22. The multi-layer conical seal 22 can include a series of overlapping seal segments 28 that are assembled in a woven arrangement to provide a complete seal body. The seal segments 28 can be stacked on top of one another or woven together in an overlapping fashion to form the multi-layer seal 22 having a central opening 30 therein. The seal segments 28 can be made from any number of materials known to those skilled in the art, but in an exemplary embodiment the seal segments 28 are formed from an elastomeric material. The seal segments 28 can also be molded such that they have a varying thickness across the profile of the seal 22. Varying the thickness across the profile of the seal 22 can be effective to minimize leakage and reduce drag forces on instruments passed therethrough. The multi-layer protective member 24 can similarly be formed from a series of overlapping segments 32 that are disposed proximal to the overlapping seal segments 28 and that are configured to protect the seal segments 28 from damage caused by surgical instruments inserted through the opening 30 in the seal 22. The protective member 24 can also be formed from various materials, but in certain exemplary embodiments the protective member 24 is formed from a molded thermoplastic elastomer. The segments 28, 32 that form the seal 22 and the protective member 24 can be held together using various techniques known in the art. As shown in FIG. 3, the segments 28, 32 are held together by several ring members that mate to engage the segments 28, 32 therebetween. In particular, the protective member 24 is engaged between a crown 34 and a gasket ring 36, and the seal 22 is engaged between the gasket ring 36 and a retainer ring 38. Pins 40 are used to mate the ring members 34, 36, 38 and to extend through and engage the segments of the seal 22 and the protective member 24.

When fully assembled, the instrument seal 18 can be disposed at various locations within the surgical access device 2. In the embodiment illustrated in FIG. 2, the instrument seal 18 is disposed in the proximal housing 4 of the surgical access device 2 at a location just distal of the proximal opening 12 and proximal of a trocar seal 20. Alternatively, or in addition, one or more seals can be positioned in the cannula 6. In use, an instrument can be inserted into the center of the seal assembly and the seal segments 28, 32 can engage and form a seal around an outer surface of the instrument to thereby prevent the passage of fluids through the seal 18. When no instrument is inserted therethrough, the opening will not form a seal in the working channel 10, however other configurations in which a seal is formed when no instrument is inserted therethrough are also conceivable. Exemplary instrument seal configurations are described in more detail in U.S. Publication No. 2004/0230161 entitled "Trocar Seal Assembly," filed on Mar. 31, 2004, and U.S. application Ser. No. 10/687, 502 entitled "Conical Trocar Seal," filed on Oct. 15, 2003, which are hereby incorporated by reference in their entireties.

The trocar or zero-closure seal 20 in the illustrated embodiment is shown in more detail in FIG. 4, and as shown the illustrated zero-closure seal is in the form of a duckbill seal 42. The seal 42 is configured to form a seal in the working channel 10 when no instrument is inserted therethrough to thus prevent the leakage of insufflation gases delivered through the surgical access device 2 to the body cavity. As shown, the duckbill seal 42 has a generally circular flange 44 with a sidewall 46 extending distally therefrom. The shape of the sidewall 46 can vary, but in the illustrated embodiment, the sidewall 46 includes opposed flaps 48 that extend at an angle toward one another in a distal direction and that come together at a distal end to form a seal face 50. The opposed flaps 48 are movable relative to one another to allow the seal face 50 to move between a closed position, in which no instrument is inserted therethrough and the seal face 50 seals the working channel 10 of the surgical access device 2, and an open position in which an instrument is inserted therethrough. The seal can include various other features, as described in more detail in U.S. application Ser. No. 11/771,263, entitled "Duckbill Seal with Fluid Drainage Feature," filed on Jun. 29, 2007, which is hereby incorporated by reference in its entirety. A variety of other duckbill-type seals are known to those skilled in the art.

In accordance with the present disclosure the general structure of the seals as well as the proximal housing do not generally form part of the present invention. As such, a person skilled in the art will certainly appreciate that various seal configurations, as well as various housings or other surgical access devices, can be used without departing from the spirit of the invention disclosed herein.

Figure 5:
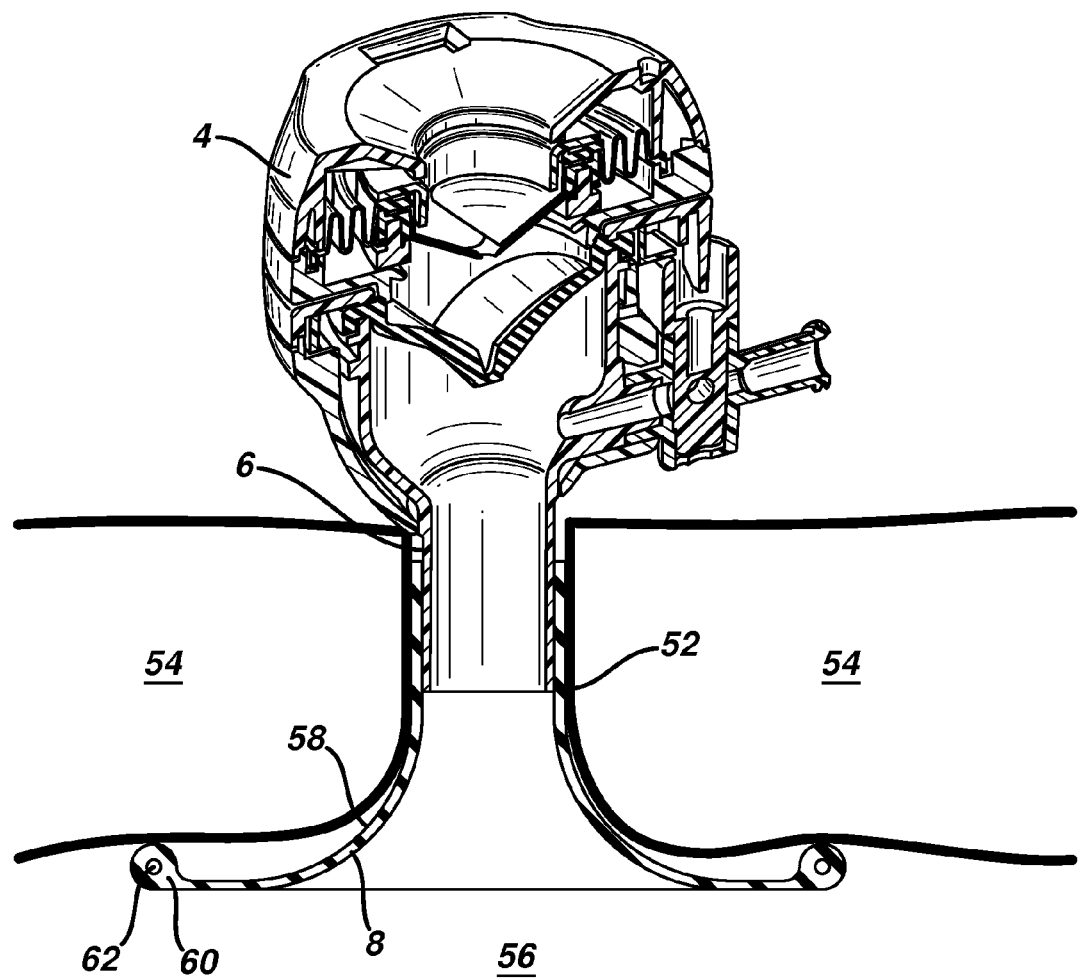
FIG. 5 is a cross-sectional view of the surgical access device of FIG. 1 inserted into an incision in a tissue layer.

In use, as shown for example in FIG. 5, the intermediate cannula 6 and the distal retractor 8 can be inserted partially through an incision or opening 52 in a tissue layer 54 to position a distal-most end of the retractor 8 within a body cavity 56. The proximal housing 4 can remain external to the body cavity, and various instruments can be inserted through the working channel 10 and into the body cavity 56.

In the embodiment illustrated in FIG. 5, the distal retractor 8 is generally in the form of an elongate, flexible, and/or elastic sleeve 58 with an annular ring 60 at its distal circumference. The annular ring 60 itself can be formed of a flexible and/or resilient material or the ring 60 can include a flexible and/or resilient member disposed therein. In the illustrated embodiment, the annular ring 60 includes a resilient and flexible member 62 in the form of a wire disposed therein. The wire can be formed from a superelastic material such as a shape memory alloy (e.g., Nitinol) or any other material known in the art having suitable flexibility and/or resiliency. One having ordinary skill in the art will appreciate that a variety of techniques can be employed for mating the resilient member 62 to the distal circumference of the sleeve 58. For example, the sleeve can be inserted within the wire, molded around the wire, or bonded thereto with an adhesive.

The elongate sleeve 58 can have a variety of shapes and sizes. In one embodiment, the sleeve is of a generally tubular shape that flares into a frustoconical shape at its distal portion. The elongate sleeve 58 can have a diameter at its proximal end in a resting state that is slightly smaller than the diameter of the distal end of the intermediate cannula 6. This allows the sleeve 58 to be stretched over the cannula 6 during manufacturing or assembly of the device and for the sleeve's elastic properties to subsequently assist in retaining the sleeve 58 in position over the cannula 6. In contrast, the elongate sleeve 58 preferably has a diameter at its distal end that is larger than the diameter of both the distal end of the cannula 6 and the proximal portion of the sleeve 58. In an exemplary embodiment, the sleeve can have a diameter at its proximal end of about 5-12 mm. The outside diameter of the distal end of the sleeve can be proportionate to the incision or puncture made in the tissue layer. For example, in one embodiment where a 5 mm incision is to be used, the device 2 can include a sleeve 58 with an outside diameter at its distal end of about 15 mm and a cannula 6 with an outside diameter of about 5 mm. In another exemplary embodiment, where a 10-12 mm incision is to be used, the device 2 can include a cannula 6 having a 10-12 mm outside diameter and a sleeve 58 having an outside diameter at its distal end of about 25 mm. The sleeve length can vary depending upon the requirements of a surgical procedure and the size of the patient. In one embodiment, the length can be about 20-30 mm for abdominal walls having a thickness less than 4 cm and about 40-60 mm for abdominal walls having a thickness of 4-7 cm. The elongate sleeve 58 can be formed from a variety of materials. For example, the sleeve 58 can be formed of silicone, polyisoprene, other elastomers or rubbers, or a combination thereof.

In another embodiment, the sleeve can be formed initially such that it has a constant-diameter cylindrical shape. The sleeve can then be mechanically strained to the diameter of the annular ring, which has a diameter greater than that of the initially cylindrical sleeve. The strain between the relaxed diameter of the sleeve and the strained diameter caused by the annular ring can give the sleeve a funnel-like shape and can apply an outward radial force on the incision through which the device is inserted, thereby providing improved retraction. In one embodiment, the magnitude of the strain (the change in diameter from the relaxed state to the strained state) can be about 100%. For example, the sleeve can be strained from a relaxed diameter of about 15 mm to a strained diameter of about 30 mm. The retraction provided by the device can be optimized by varying the magnitude of the strain and the modulus of the sleeve material. In an exemplary embodiment, the strain magnitude can be about 70% to about 120%. In another embodiment, the strain magnitude can be about 5% to about 500% and in a still further embodiment the strain magnitude can be 1% or more. The upper limit on the amount of strain that is possible depends on the modulus of the sleeve material and the modulus of the annular ring. As will be discussed further below, this outward force of the sleeve pressing against the inner walls of the incision and pulling the annular ring upward against the inner abdominal wall can advantageously provide a tight seal between the device and the surrounding tissue.

Figure 6:
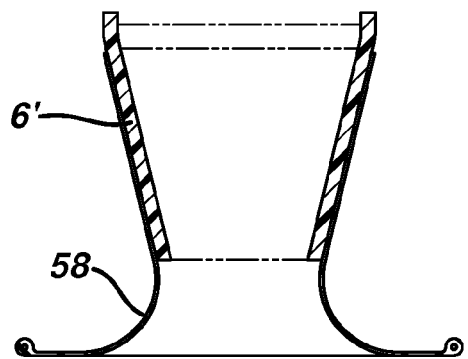
FIG. 6 is a cross-sectional view of a distal portion of one embodiment of a surgical access device having a tapered cannula.
Figure 7A:
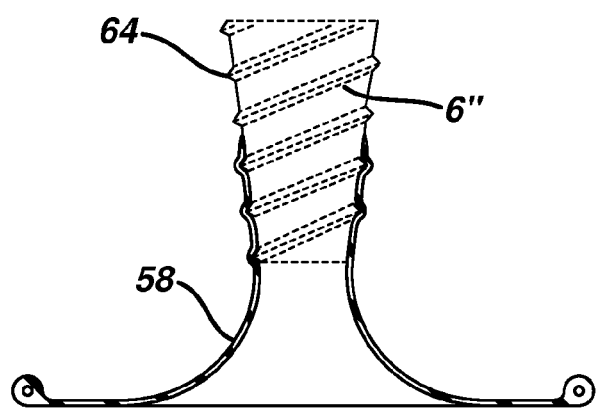
FIG. 7A is a cross-sectional view of a distal portion of one embodiment of a surgical access device having a cannula with a helical thread formed on an exterior surface thereof.
Figure 7B:
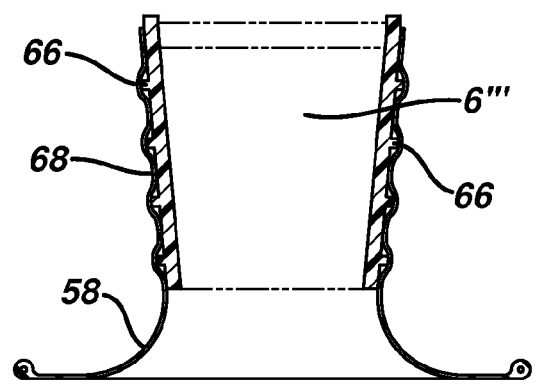
FIG. 7B is a cross-sectional view of a distal portion of one embodiment of a surgical access device having a cannula with a plurality of raised ridges formed on an exterior surface thereof.

The retractor 8 can be mated to the cannula 6 in a variety of ways. In one embodiment, as shown in FIG. 5 and discussed above, the elongate sleeve 58 of the retractor 8 can simply be stretched over the distal end of the cannula 6 and remain mated thereto by the elastic properties of the sleeve 58 and the frictional forces associated therewith. In another embodiment, as shown in FIG. 6, the distal end of the cannula 6' can be tapered from its proximal end to its distal end such that its outer and/or inner diameters gradually decrease as the distal end of the cannula is approached. The taper can be at a constant slope (as illustrated) or can occur in intermittent steps. The tapered outer surface of the cannula 6' can facilitate stretching of the sleeve 58 thereover during manufacturing or assembly of the device. In another embodiment, the cannula can include one or more surface features formed on an exterior thereof configured to engage the sleeve. As shown in FIG. 7A, a helical thread 64 can be formed on the exterior of the cannula 6" to provide further engagement with the sleeve 58. Alternatively, or in addition, one or more raised ridges 66 can be formed on the exterior of the cannula 6''' as shown in FIG. 7B. In the illustrated embodiment, the sleeve 58 has elastic properties that cause it to conform closely with the exterior surface of the cannula 6''', stretching into the channels 68 between adjacent raised ridges 66.

Figure 8A:
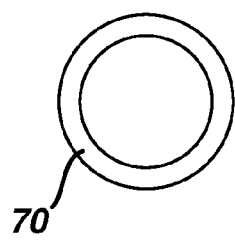
FIG. 8A is a plan view of one embodiment of a collar comprising an elastic o-ring.

One or more collars can also be used to assist in mating the sleeve 58 to the cannula 6. FIG. 8A depicts one exemplary collar in the form of an elastic o-ring 70. The elastic o-ring 70 can be sized such that it is configured to be disposed around the sleeve 58 and the cannula 6 and to apply elastic pressure thereto. The elastic pressure exerted by the o-ring 70 buttresses the elasticity of the sleeve 58 itself, thereby forming a stronger mating between the sleeve 58 and the cannula 6.

Figure 8B:
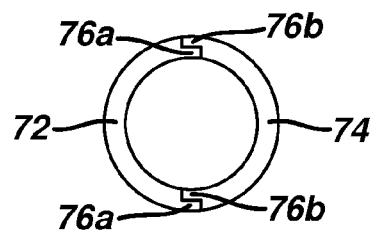
FIG. 8B is a plan view of one embodiment of a collar comprising two matable halves.
Figure 8C:
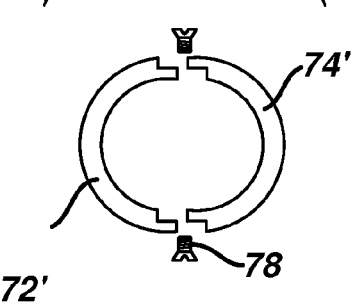
FIG. 8C is an exploded plan view of one embodiment of a collar comprising two halves matable by screws.

FIG. 8B depicts one embodiment of a collar that comprises two matable halves 72, 74. The first collar half 72 can include tabs 76a on each of its ends that are configured to mate with corresponding tabs 76b on each end of the second collar half 74. The tabs can be mated using any of a variety of methods known in the art, such as snap-fitting, sonic welding, gluing, riveting, and so forth. FIG. 8C depicts a similar embodiment in which a plurality of screws 78 are used to mate the first and second collar halves 72', 74'. As shown, the screws can have flat heads to facilitate countersinking within the collar halves so that no portion of the screw protrudes beyond the outer diameter of the collar, which could interfere with or irritate a tissue layer in which the device is inserted. The screws can have a length that is about equal to the thickness of the collar, or can optionally have a greater length such that the screw pierces the sleeve and engages the underlying cannula. In certain embodiments, the matable collar halves 72, 74 are configured to be separated and reattached easily to permit on-the-fly swapping of the components of the surgical access device. For example, if a first retractor becomes damaged, soiled, or is of inappropriate size, a surgeon can remove any collars mating it to the cannula, replace the first retractor with a second retractor, and reattach the collar(s). While the illustrated embodiment includes two matable halves, the collar can alternatively be formed of a single deformable piece that snaps together at a single joint, or from any number of separate collar components, for example three-, four-, or five-piece collars.

Figure 8D:
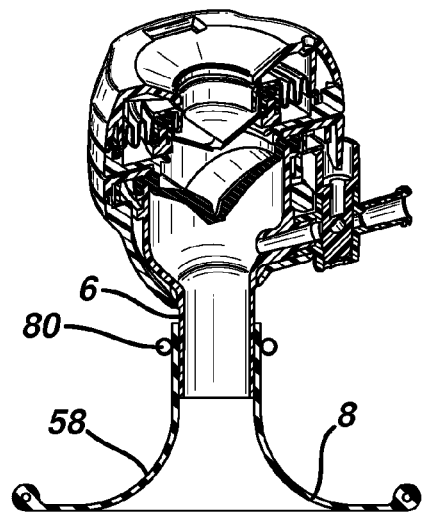
FIG. 8D is a cross-sectional view of the surgical access device of FIG. 1 having a collar disposed around the flexible retractor and a cannula.
Figure 8E:
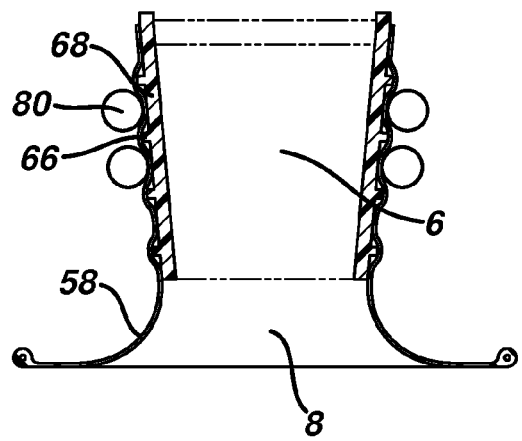
FIG. 8E is a cross-sectional view of the distal portion of the surgical access device of FIG. 7B having multiple collars disposed around a retractor and the cannula.

FIG. 8D illustrates a cross-sectional view of the surgical access device of FIG. 2 with the addition of a collar 80. As shown, the collar 80 can be disposed around both the cannula 6 and the sleeve 58 of the retractor 8 to assist in mating the two structures. Similarly, FIG. 8E illustrates a cross-sectional view of the surgical access device of FIG. 7B with the addition of multiple collars 80. In the illustrated embodiment, the collars 80 are positioned over the channels 68 between the adjacent raised ridges 66 formed on the exterior of the cannula 6. The collars 80 can be seen to pinch the sleeve 58 down into the channels 68, thereby supplying additional engagement strength between the retractor 8 and the cannula 6.

Figure 9A:
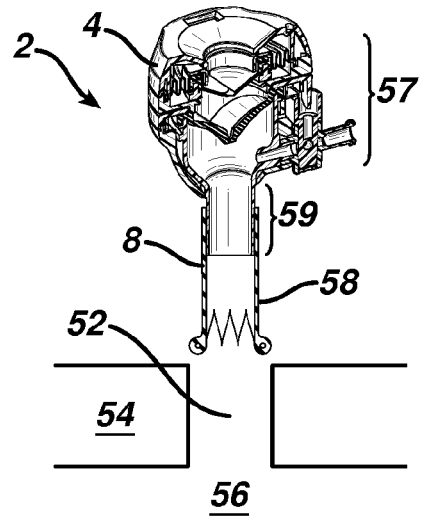
FIG. 9A is a cross-sectional view of an incised tissue layer and the surgical access device of FIG. 1 with a retractor in a deformed state.
Figure 9B:
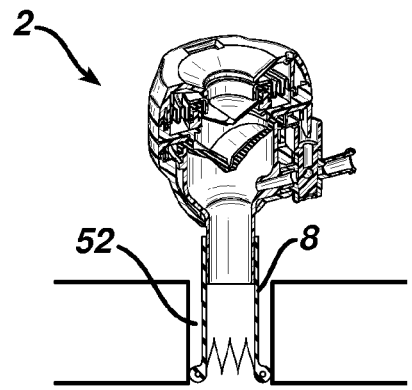
FIG. 9B is a cross-sectional view of the surgical access device of FIG. 9A partially inserted into the incised tissue layer.
Figure 9C:
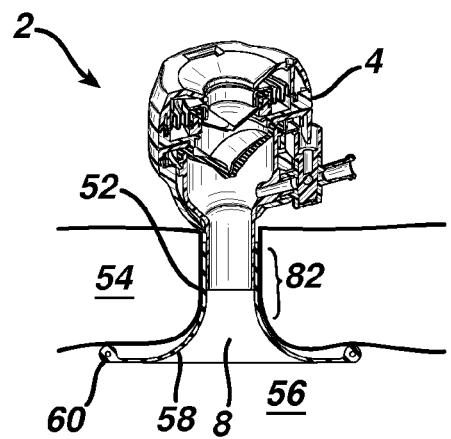
FIG. 9C is a cross-sectional view of the surgical access device of FIG. 9A with the retractor in an undeformed state beneath the incised tissue layer of FIG. 9A.

In use, the surgical access device can be utilized in various methods for providing access through tissue to a body cavity. In one embodiment, as shown in FIGS. 9A-9C, an incision 52 can be made in a tissue layer 54 to access a body cavity 56. A surgical access device 2 can be provided having a housing 4 with an external portion 57 and an elongate implantable portion 59 (also referred to herein as a cannula 59 or a cannula portion 59). The cannula portion 59 is mated to a flexible and/or resilient retractor 8 with a distal end having a diameter in its undeformed state that is larger than the diameter of the incision 52. The retractor 8 can then be deformed, as shown in FIG. 9A, such that the distal end of the retractor 8 has a diameter substantially the same as or less than that of the incision 52. The retractor 8 can be deformed in a variety of ways, for example by manually folding or squeezing the distal end thereof (i.e., by hand or using an instrument). Alternatively, or in addition, a temporary adhesive can be applied to an interior or exterior surface of the retractor 8 to maintain the retractor 8 in a folded position during insertion into the incision 52. Once the surgical access device 2 is inserted in the incision 52, passage of a surgical instrument therethrough can separate the adhered portions of the retractor 8, thereby permitting it to flare outwards towards its undeformed state. In another embodiment, the surgical access device 2 can be initially provided with an obturator positioned within the working channel 10. The distal end of the retractor 8 can be temporarily attached or coupled to the obturator using any of a variety of fastening means known in the art such that the retractor 8 is retained in a deformed state. Once the surgical access device 2 is inserted in the incision 52, the obturator can be withdrawn proximally, releasing the retractor 8 and allowing it to flare outwards towards its undeformed state. One having ordinary skill in the art will appreciate that a variety of other techniques for deforming the retractor 8 during insertion into the incision 52 are possible, for example by using a draw string, one or more magnets or electromagnets, and so on.

FIG. 9B shows the surgical access device 2 partially inserted into the incision 52, with the retractor 8 still in a deformed state. FIG. 9C shows the surgical access device 2 of FIG. 9B advanced further distally into the incision 52, such that the distal end of the retractor 8 extends beyond the distal surface of the tissue layer 54. Once so positioned, the retractor 8 can be allowed to return to its undeformed state or to approach its undeformed state. As shown, being no longer restrained by the confines of the incision 52 (or by any of the optional deformation techniques described above), the resilient annular ring 60 can be free to expand to or otherwise passively return to or approach its undeformed state, thereby causing the elongate sleeve 58 of the flexible retractor 8 to assume its flared or funnel-like shape.

The force applied to the elongate sleeve 58 by the resiliency of the annular ring 60 can pull the sleeve laterally against the sidewalls of the incision 52 to form a seal region 82. The seal region 82 can provide a substantially fluid-tight seal between the surgical access device 2 and the incision 52. Because of the flexible and/or resilient nature of the elongate sleeve 58 and/or the annular ring 60, this seal can be substantially maintained even during extreme flexion or angulation of the surgical access device 2 with respect to the tissue layer 54. The seal region 82 can thus permit a broader range of surgical maneuvers without compromising insufflation pressure within the body cavity 56.

The seal region 82 can exist at a variety of locations along the length of the cannula portion 59 and/or the retractor 8. In one embodiment, the seal region 82 is located at the distal-most end of the cannula 59 and the immediate vicinity thereof, where the surgical access device 2 effectively transitions from the semi-rigid cannula 59 and housing 4 to the flexible retractor 8. The seal region 82 can also include the entire region where the elongate sleeve 58 overlaps the cannula 59, which in an exemplary embodiment can be about 3 mm to about 15 mm in length. The seal region can also be approximately equal to the thickness of the tissue layer 54, which can be about 12 mm to about 100 mm or more in abdominal procedures. In such embodiments, the seal region can extend along both the region where the sleeve 58 overlaps the cannula 59 and the region distal thereto where the sleeve 58 extends beyond the cannula 59. In one embodiment, the seal region can have a length in the range of about 1 to about 200 mm. In another embodiment, the seal region length can be in the range of about 10 to about 100 mm and in a still further embodiment the seal region can have a length in the range of about 3 to about 15 mm. In an exemplary embodiment, the surgical access device 2 is sized such that the cannula-retractor transition point and/or seal region 82 is positioned within the tissue layer 54, and in one embodiment, positioned approximately midway through the tissue layer 54 when the access device 2 is fully inserted. For example, the distal-most end of the cannula 59 can be positioned approximately halfway between the exterior and interior surfaces of the tissue layer 54.

As also shown in FIG. 9C, once the retractor 8 is deployed within a body cavity 56, its flexibility/resiliency can permit the annular ring 60 to abut and be in direct contact with the interior surface of the tissue layer 54. As also shown, the distal end of the housing 4 can at the same time abut and be in direct contact with the external surface of the tissue layer 54. As can be seen by comparing the incision prior to deployment of the retractor 8 (as shown in FIG. 9B) to the incision post-deployment (as shown in FIG. 9C), the retractor 8 serves to retract the distal portion of the tissue layer further than would existing straight cannulas known in the art. Furthermore, the positioning of the resilient annular ring 60 beneath the tissue layer 54 and in contact therewith can stabilize and improve retention of the access device 2 within the opening 52.

Figure 10:
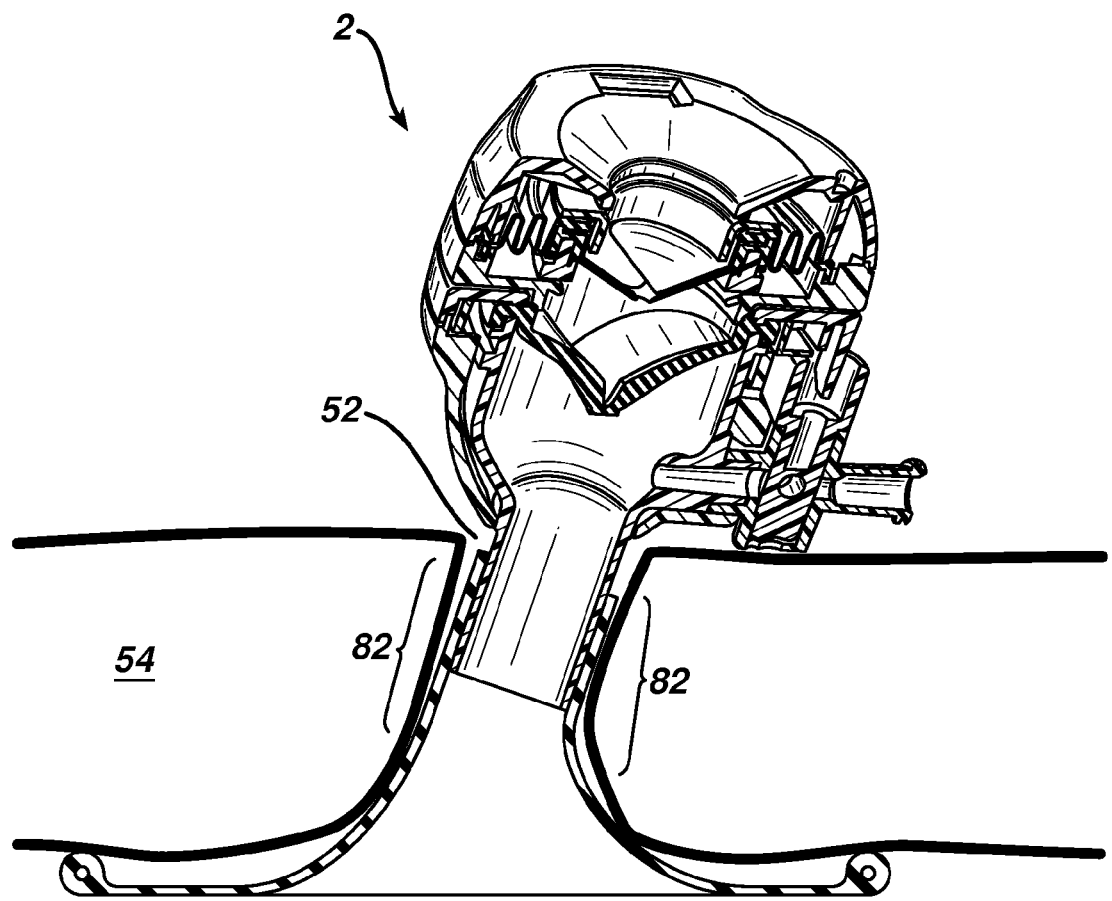
FIG. 10 is a cross-sectional view of the surgical access device of FIG. 1 having been angulated within an incision in a tissue layer.

FIG. 10 illustrates a surgical access device 2 positioned at an angle with respect to a tissue layer 54 having an incision 52 formed therein. As shown, the seal region 82 can act to maintain a substantially fluid-tight seal between the surgical access device 2 and the sidewalls of the incision 52, despite the angulation of the device.

The surgical access device 2 can be removed from the opening 52 in a variety of ways. In one exemplary method, the surgeon can simply pull the housing proximally from the opening 52, causing the retractor 8 to stretch and deform until it ultimately is capable of passing through the opening 52. In another embodiment, the surgeon can use surgical instruments such as graspers, clips, sutures, etc. to deform the retractor to, and/or hold the retractor in a smaller profile prior to withdrawing the access device 2 proximally from the opening 52.

Figure 11A:
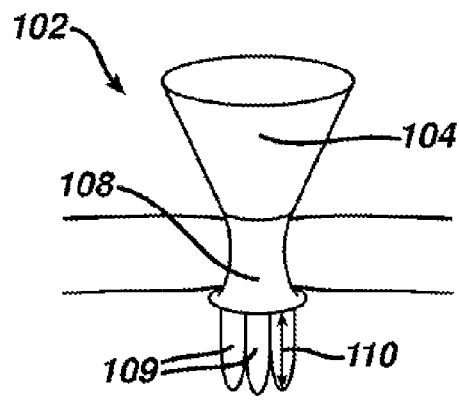
FIG. 11A is a partial cross-sectional view of one embodiment of a surgical access device having peel-away cannulas inserted into an incised tissue layer.

FIG. 11A depicts another embodiment of a surgical access device 102. As shown, the surgical access device 102 is generally in the form of a housing having an external funnel-shaped proximal portion 104 (also referred to herein as an external housing), an intermediate flexible retractor 108, and one or more flexible cannulas 109 extending distally from the external housing 104 and through the intermediate retractor 108. Each flexible cannula 109 defines a working channel 110 that is in communication with a funnel-shaped working channel defined by the external housing 104 for introducing various instruments into a body cavity.

The flexible cannulas 109 are generally in the form of elongate tubular sleeves that extend distally from a plate 111 (shown in FIG. 11C) at the distal end of the external housing 104. The plate 111 can be semi-rigid or it can be flexible. The flexible cannulas 109 can be provided initially as being bonded together to facilitate insertion through an opening in a tissue layer. Upon insertion, a frangible portion and/or a temporary adhesive bond can be broken to allow the cannulas 109 to "peel away" from one another into separate, independently moveable structures.

Figure 11B:
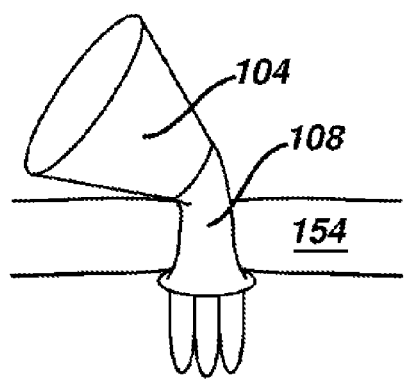
FIG. 11B is a partial cross-sectional view of the surgical access device of FIG. 11A having been angulated within the incised tissue layer.

The intermediate flexible retractor 108 can alleviate forces at the incision joint when substantial angulation and/or flexion of the surgical access device 102 is needed. As shown for example in FIG. 11B, the external housing 104 can be angulated significantly with respect to a tissue layer 154 without any appreciable simultaneous angulation of the intermediate retractor 108. Since a substantial portion of the retractor 108 can remain at an angle roughly transverse to the tissue layer 154, the forces applied to the tissue layer during angulation of the external housing 104 are reduced.

Figure 11C:
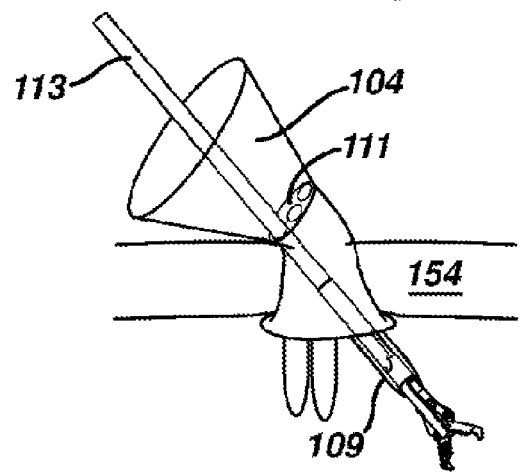
FIG. 11C is a cross-sectional view of the surgical access device of FIG. 11A with an instrument inserted therethrough.

Utilizing both a flexible intermediate retractor 108 and one or more flexible cannulas 109 allows passage of surgical instruments through the access device 102 at extreme angles while minimizing forces exerted on the tissue opening 152 in which the access device 102 is inserted. In FIG. 11C, a laparoscopic grasping tool 113 is shown inserted through a surgical access device 102 at a significant angle with respect to a tissue layer 154. As shown, the external housing 104 and cannula 109 are similarly angulated, while the retractor 108 remains in a substantially upright position, transverse to the tissue layer 154.

Figure 12A:
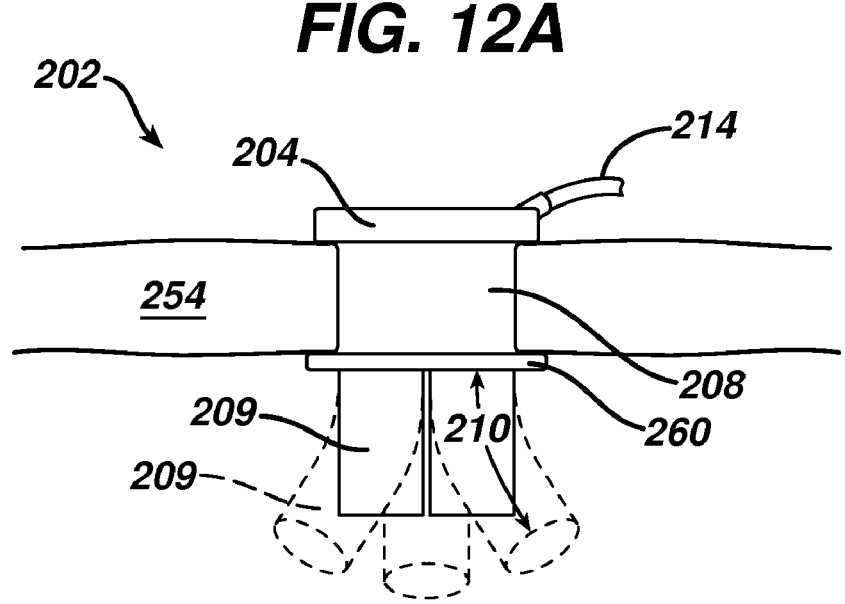
FIG. 12A is a partial cross-sectional view of one embodiment of a surgical access device having a low-profile external housing inserted into an incised tissue layer.
Figure 12B:
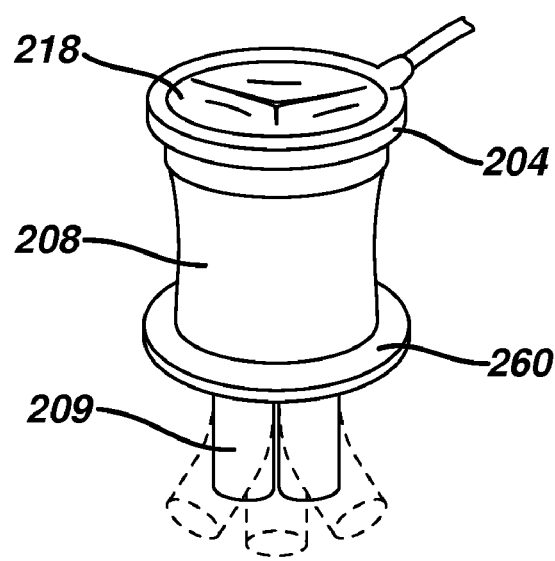
FIG. 12B is a perspective view of the surgical access device of FIG. 12A.

FIGS. 12A and 12B illustrate one embodiment of a low-profile surgical access device 202. The device 202 can comprise a low-profile external housing 204 coupled to an intermediate protective retractor 208 and one or more distal "peel-away" cannulas 209. Each cannula 209 defines a working channel 210 that is in communication with one or more working channels defined by the retractor 208 and/or the external housing 204. The low-profile external housing 204 can include an insufflation port 214 for communicating an insufflation fluid to or from a body cavity via the access device 202. The external housing 204 can also include one or more seals 218 configured to provide a fluid tight seal within the working channel(s) 210 defined by the cannula(s) 209 or the working channel(s) defined by the retractor 208 and/or the external housing 204. Like in the various embodiments described above, the retractor 208 can be flexible and/or resilient and can include a flexible and/or resilient annular ring 260 at its distal circumference.

As indicated by the dashed lines in FIGS. 12A and 12B, the distal cannulas 209 are flexible and can be initially provided in a joined-together configuration to facilitate insertion of the access device 202 into an incision or opening in tissue. Once the access device 202 is fully inserted, or at any other time desired by a surgeon or surgical assistant, the distal cannulas 209 can be peeled away from one another, for example by passing one or more instruments therethrough and then spreading the instruments to separate the cannulas 209.

Figure 13A:
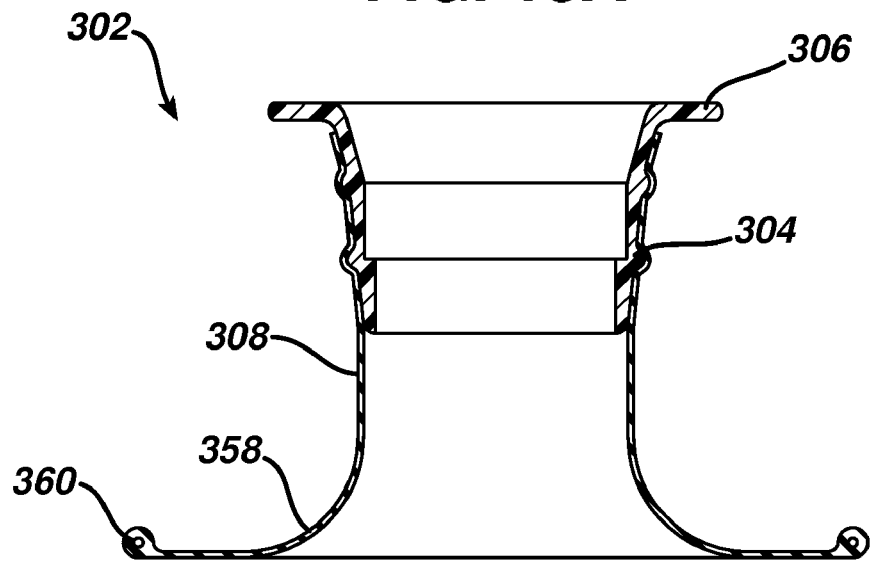
FIG. 13A is a cross-sectional view of one embodiment of a flat-port surgical access device.

FIG. 13A illustrates a flat-port access device 302 modified to include a flexible and/or resilient retractor 308 at its distal end with a flexible and/or resilient annular ring 360 at the distal circumference of the retractor 308. A length of the retractor 308 overlaps the distal end of the access device 302 and one or more retention rings 304 can be formed on an exterior surface of the device 302 to assist in retaining the retractor 308. In the illustrated embodiment, the elongate sleeve portion 358 of the retractor 308 extends to a point just distal to the proximal lip 306 of the device 302. As shown, the device 302 can be provided without any tie-down features at the its proximal lip 306, since the retractor 308 can provide adequate retention of the device 302 within a tissue opening.

Figure 13B:
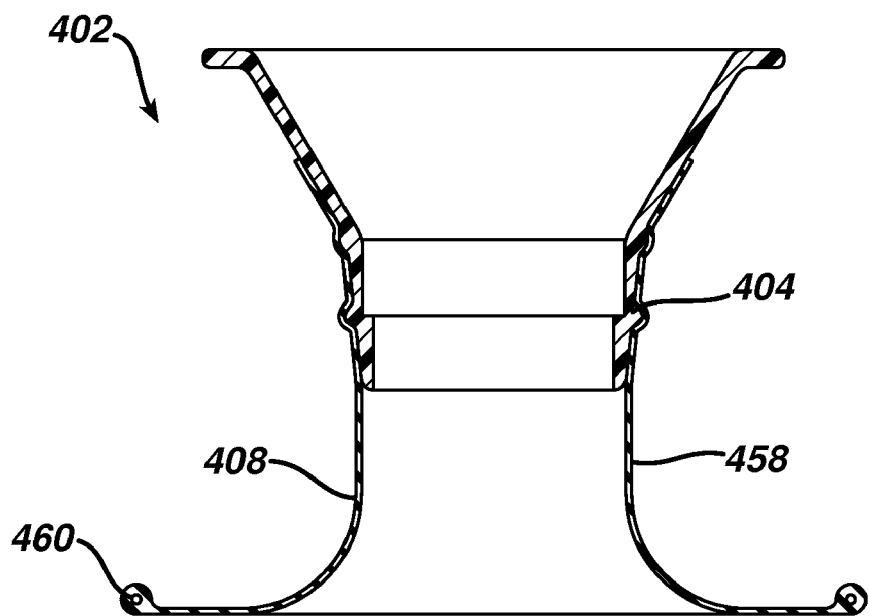
FIG. 13B is a cross-sectional view of one embodiment of a funnel-port surgical access device.

FIG. 13B illustrates one embodiment of a funnel-port access device 402 modified to include a retractor 408 and annular ring 460 similar to that described above with respect to the flat-port access device of FIG. 13A. As shown, the elongate sleeve portion 458 of the retractor 408 can extend over one or more retention rings 404 formed on the exterior surface of the device 402 and over at least a portion of the funnel-shaped proximal end of the device 402.

Figure 14A:
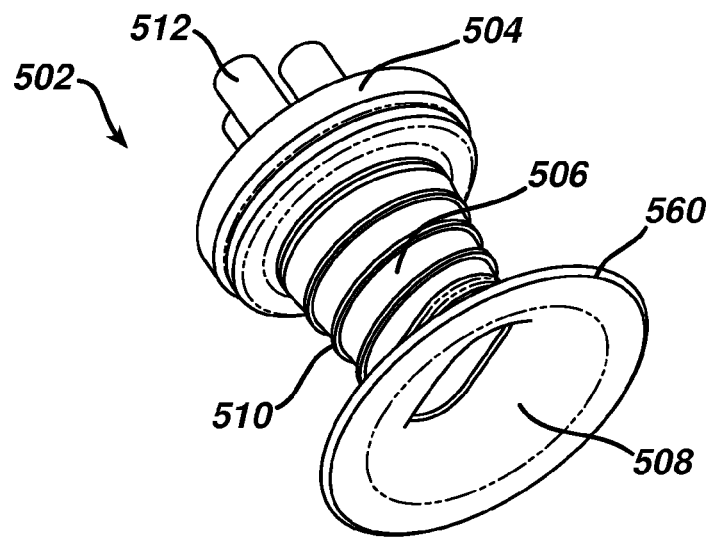
FIG. 14A is a perspective view of one embodiment of an obround-port surgical access device.
Figure 14B:
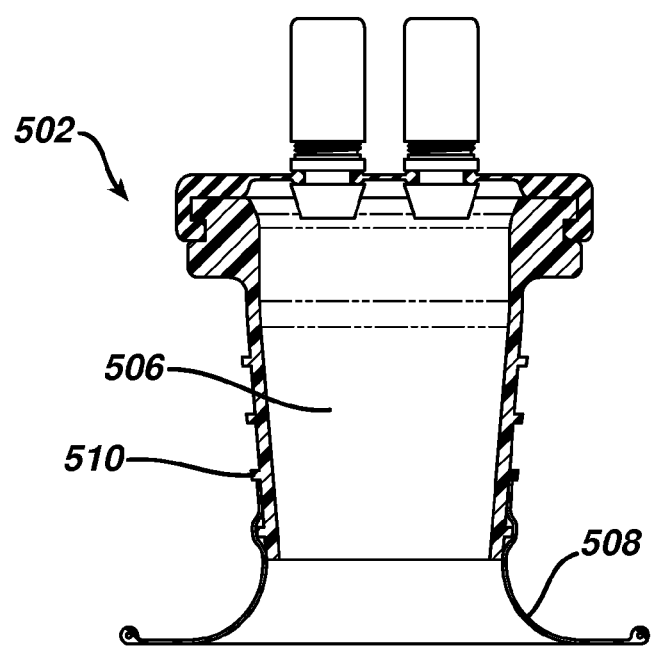
FIG. 14B is a cross-sectional view of the surgical access device of FIG. 14A.
Figure 14C:
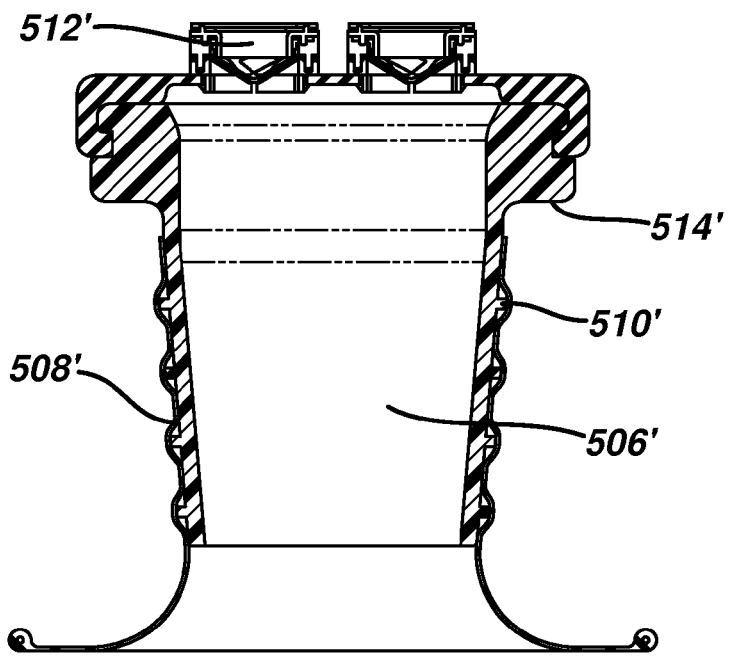
FIG. 14C is a cross-sectional view of another embodiment of a surgical access device.
Figure 14D:
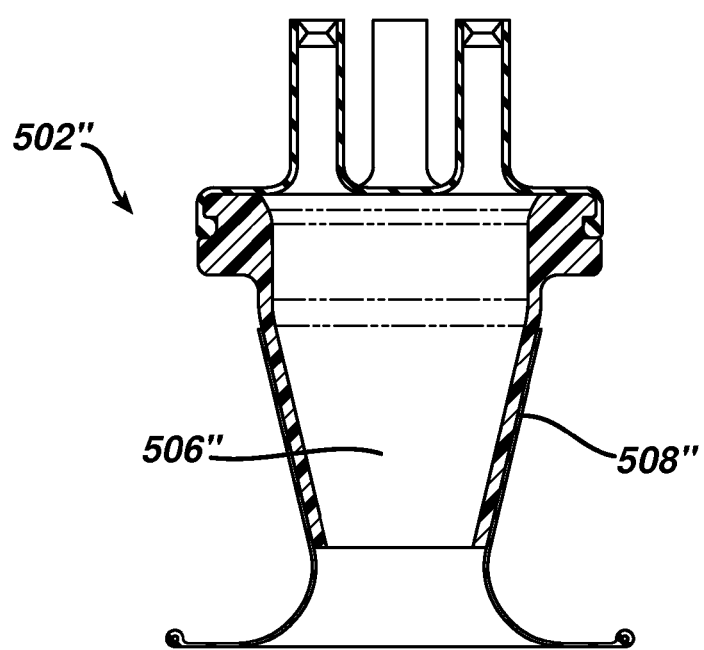
FIG. 14D is a cross-sectional view of another embodiment of a surgical access device.

FIG. 14A illustrates one embodiment of an obround-port access device 502. The device 502 can include a cannula portion 506 and a housing 504. The housing 504 can have one or more valves or one or more sealed instrument ports 512 therein and can be in the form of a removable top that is separable from the cannula portion 506. The cannula portion 506 can have one or more retention rings 510 formed on an exterior thereof. As shown, the device 502 can be modified to include a retractor 508 and annular ring 560 as described above. The retention functionality provided by the retractor 508 and annular ring 560 can obviate the need for additional tie-down features on the housing 504 or the cannula portion 506. FIGS. 14B-14D illustrate cross-sectional views of several variations of the device 502 of FIG. 14A. As shown in FIG. 14B, the retractor 508 can overlap the distal portion of the cannula portion 506 and the retention rings 510 formed thereon can assist in retaining the retractor 508. As shown in FIG. 14C, the device 502' can include one or more instrument ports 512' having so-called "pac man" seals disposed therein. As also shown, the retractor 508' can extend proximally to a location just distal to a lip 514' at the proximal end of the cannula portion 506', thereby overlapping a significant length of the cannula portion 506' and facilitating engagement of the retractor 508' by a plurality of retention rings 510'. FIG. 14D illustrates an alternative embodiment of an access device 502" having a cannula portion 506" with a more exaggerated taper. In addition, the cannula portion 506" has no retention rings formed thereon and instead relies on alternative means of retaining the retractor 508". Such means can include any of those discussed above (i.e. frictional engagement or an adhesive) or can include any other suitable means known in the art.

Figure 15A:
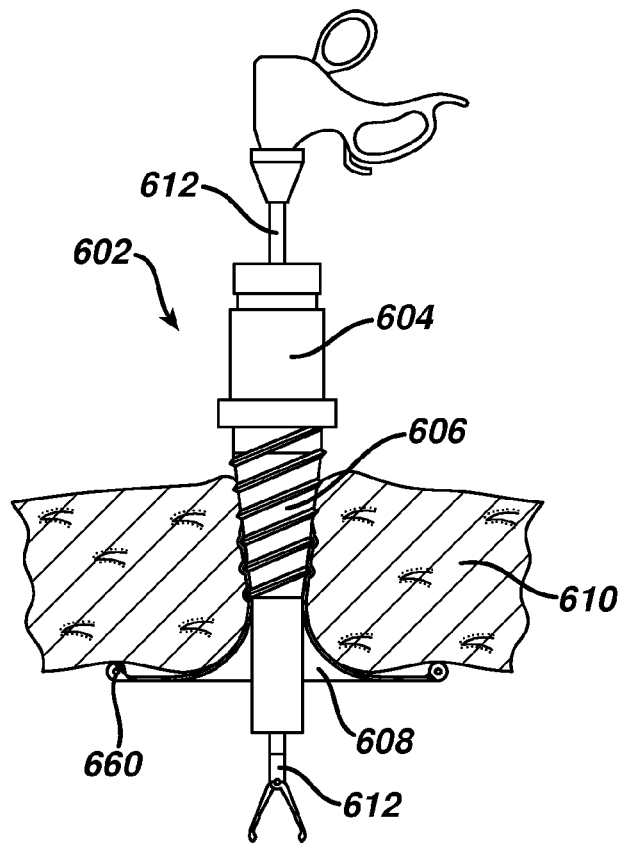
FIG. 15A is a partial cross-sectional view of one embodiment of a surgical access device with a tapered threaded cannula inserted through a tissue layer.

FIGS. 15A-D illustrate additional embodiments of a surgical access device. In FIG. 15A, an access device 602 is shown having an external housing 604, an implantable semi-rigid cannula 606, and a distal retractor 608. Like in several of the aforementioned embodiments, the retractor 608 can be flexible and/or resilient and can include a flexible and/or resilient annular ring 660 at its distal circumference. The access device 602 of FIG. 15A is shown inserted through a tissue layer 610 and with a laparoscopic grasping tool 612 disposed in a working channel formed therethrough. As shown, the cannula 606 can include one or more surface features on all or a portion of its exterior configured to help retain the retractor 608 over the cannula 606 and to help retain the access device 602 within the tissue layer 610. The cannula 606 can be tapered such that it has a diameter at its proximal end that is greater than the diameter at its distal end.

Figure 15B:
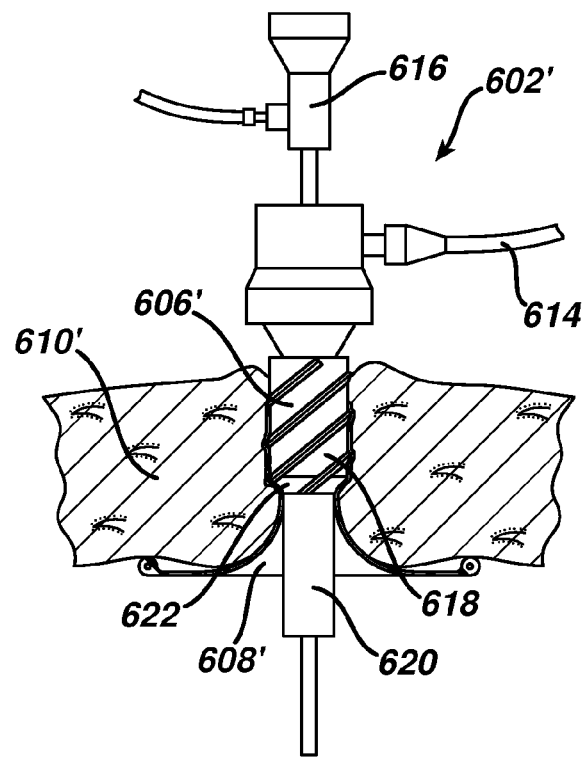
FIG. 15B is a partial cross-sectional view of one embodiment of a surgical access device with a cylindrical threaded cannula inserted through a tissue layer.
Figure 15C:
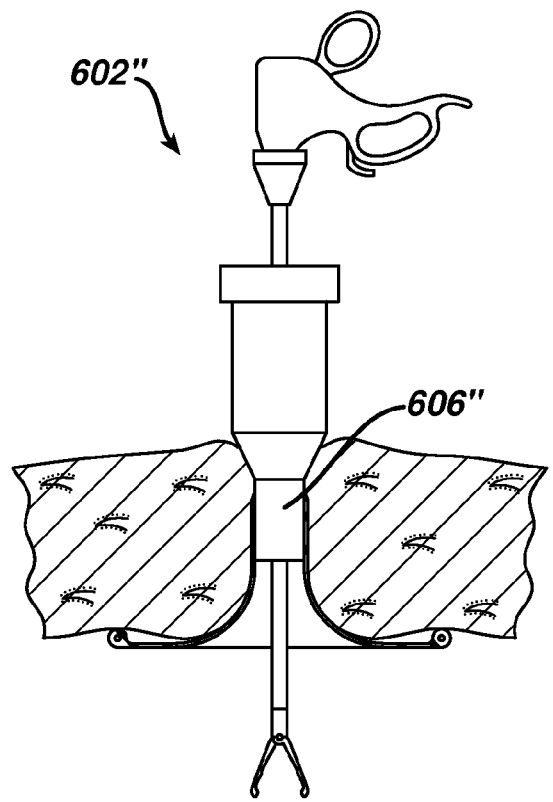
FIG. 15C is a partial cross-sectional view of one embodiment of a surgical access device with a cylindrical smooth cannula inserted through a tissue layer.

FIG. 15B depicts another embodiment of a surgical access device 602' operatively coupled to an insufflation source via an insufflation tube 614 and having a viewing scope 616 disposed in a working channel formed therethrough. Rather than having a gradual taper as in some previously described embodiments, the implantable semi-rigid cannula 606' in the illustrated embodiment has a generally cylindrical shape that transitions from a larger diameter upper portion 618 to a smaller diameter lower portion 620 at a tapered shoulder region 622. As shown, the upper cannula portion 618 and the shoulder region 622 can have one or more surface features formed thereon and configured to help retain the retractor 608' over the cannula 606' and to help retain the access device 602' within the tissue layer 610'. Alternatively, as shown in FIG. 15C a surgical access device 602" can have a cannula 606" with a generally smooth, feature-less exterior surface.

Figure 15D:
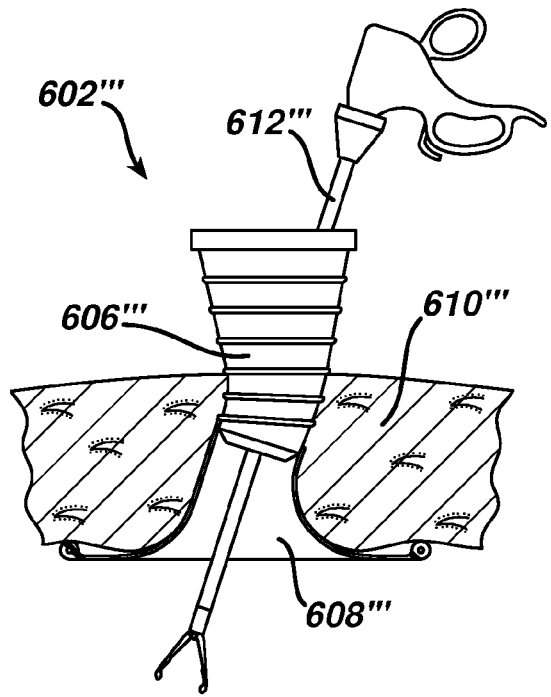
FIG. 15D is a partial cross-sectional view of one embodiment of a surgical access device with a funnel-shaped threaded cannula having been implanted and angulated within a tissue layer.

FIG. 15D shows another embodiment of a surgical access device 602'". The device 602'" includes a semi-rigid, implantable, funnel-shaped cannula 606'" and a distal retractor 608'". As shown, the semi-rigid properties of the cannula 606'" can permit at least some degree of flexion along a length of the cannula 606'". The flexible and/or elastic properties of the retractor 608'" allow a seal between the device 602'" and the surrounding tissue layer 610'" to be maintained despite the flexion of the cannula 606'" and the angulation of a surgical instrument 612'" passed through a working channel thereof.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical access device, comprising:
    a housing having a proximal external portion and an elongate implantable distal portion with at least one working channel extending therebetween, the housing being configured to receive at least one surgical instrument for passage into the working channel;
    a flexible elongate sleeve coaxial with the housing and matable to and extending over a portion of the implantable distal portion such that the sleeve extends distally from the implantable distal portion; and
    a resilient and flexible annular ring at the distal circumference of the sleeve, wherein the annular ring has a diameter in its undeformed state that is greater than a diameter of the sleeve and the implantable distal portion, such that the annular ring mechanically strains a portion of the elongate sleeve such that the elongate sleeve applies an outward radial force to an inner wall of an incision when the annular ring is in its undeformed state;
    wherein the magnitude of the strain applied to the elongate sleeve by the annular ring is between about 5 percent and about 500 percent.

2. The device of claim 1, wherein the implantable distal portion has at least one surface feature on an exterior thereof that is configured to engage the sleeve.

3. The device of claim 2, wherein the at least one surface feature is at least one of a thread and a raised ridge.

4. The device of claim 1, further comprising at least one collar configured to be disposed around the sleeve and the implantable distal portion to assist in mating the sleeve to the housing.

5. The device of claim 4, wherein the at least one collar comprises an elastic o-ring.

6. The device of claim 4, wherein the at least one collar comprises two matable halves.

7. The device of claim 1, wherein the housing includes at least one instrument port formed therein, the at least one instrument port being in communication with the working channel and having at least one seal element formed therein.

8. The device of claim 7, wherein the at least one seal element is effective to provide a substantially fluid tight seal with a surgical instrument when the surgical instrument is present in the instrument port.

9. The device of claim 7, wherein the at least one seal element is effective to provide a substantially fluid tight seal when the surgical instrument is not present in the instrument port.

10. The device of claim 1, wherein the annular ring causes a distal portion of the elongate sleeve to flare outward such that it has a diameter greater than a diameter of a proximal portion of the elongate sleeve.

11. The device of claim 1, wherein the annular ring includes a resilient member disposed therein.

12. The device of claim 1, wherein the magnitude of the strain applied to the elongate sleeve by the annular ring is between about 70 percent and about 120 percent.

13. The device of claim 1, wherein the magnitude of the strain applied to the elongate sleeve by the annular ring is about 100 percent.

* * * * *